(12) United States Patent
Demas et al.

(10) Patent No.: US 10,349,870 B1
(45) Date of Patent: Jul. 16, 2019

(54) MAGNETIC SWITCHING

(71) Applicant: Verily Life Sciences LLC, Mountain View, CA (US)

(72) Inventors: Vasiliki Demas, San Jose, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 961 days.

(21) Appl. No.: 14/861,822

(22) Filed: Sep. 22, 2015

Related U.S. Application Data

(60) Provisional application No. 62/053,334, filed on Sep. 22, 2014.

(51) Int. Cl.
- *A61B 5/145* (2006.01)
- *A61B 5/00* (2006.01)
- *A61B 5/05* (2006.01)

(52) U.S. Cl.
CPC .............. *A61B 5/145* (2013.01); *A61B 5/05* (2013.01); *A61B 5/6801* (2013.01)

(58) Field of Classification Search
CPC ............... A61N 2/002; A61B 5/14532; A61B 5/14546; A61B 5/1486; A61B 5/14539; A61B 5/0031

See application file for complete search history.

(56) References Cited

U.S. PATENT DOCUMENTS 5,305,751 A * 4/1994 Chopp ................. A61B 5/0265
600/409
5,978,694 A * 11/1999 Rapoport ............... G01R 33/16
600/309

(Continued)

FOREIGN PATENT DOCUMENTS

| WO | 2011053435 A1 | 5/2011 |
| WO | 2013030601    | 3/2013 |

(Continued)

OTHER PUBLICATIONS

International Searching Authority, International Search Report and Written Opinion for International Application No. PCT/US2014/054321 dated Dec. 17, 2014, 14 pages.

(Continued)

*Primary Examiner* — Eric F Winakur
(74) *Attorney, Agent, or Firm* — McDonnell Boehnen Hulbert & Berghoff LLP

(57) ABSTRACT

Methods of exerting magnetic forces to collect and manipulate magnetic particles disposed in a portion of subsurface vasculature using a wearable device are provided. The wearable device is configured to change the exerted magnetic force over time. For example, the exerted magnetic force could be sufficient to collect the magnetic particles during a first period of time and low enough to release the magnetic particles during a second period of time. The exerted magnetic force could be changed over time to vary some effect on the magnetic particles, for example to control a rate of release of collected magnetic particles. In some embodiments, the magnetic particles are configured to bind to an analyte of interest. The collection and manipulation of the magnetic particles can enable detection of one or more properties of the analyte, modification of the analyte, and/or extraction of the analyte bound to the magnetic particles.

16 Claims, 11 Drawing Sheets

(56) References Cited

U.S. PATENT DOCUMENTS

| | | | |
|---|---|---|---|
| 5,981,297 A | 11/1999 | Baselt | |
| 6,292,680 B1 | 9/2001 | Somogyi et al. | |
| 6,315,709 B1 * | 11/2001 | Garibaldi | A61B 17/12022 600/12 |
| 6,623,983 B1 | 9/2003 | Terstappen et al. | |
| 7,214,190 B1 | 5/2007 | Wilson | |
| 7,448,389 B1 * | 11/2008 | Kotha | A61K 9/0009 128/898 |
| 7,817,254 B2 | 10/2010 | Hegyi et al. | |
| 7,817,276 B2 | 10/2010 | Kiesel et al. | |
| 7,844,314 B2 | 11/2010 | Al-Ali | |
| 7,894,068 B2 | 2/2011 | Bassler et al. | |
| 7,951,061 B2 | 5/2011 | Foreman et al. | |
| 8,153,949 B2 | 4/2012 | Kiesel et al. | |
| 8,344,731 B2 | 1/2013 | Lee | |
| 8,368,396 B2 | 2/2013 | Ueda | |
| 8,368,402 B2 | 2/2013 | Lee et al. | |
| 8,409,415 B2 | 4/2013 | Liu | |
| 8,529,428 B2 | 9/2013 | Creighton | |
| 8,569,044 B2 | 10/2013 | Hoon | |
| 8,624,592 B2 | 1/2014 | Lee | |
| 8,697,029 B2 | 4/2014 | Anker et al. | |
| 2004/0259270 A1 | 12/2004 | Wolf | |
| 2005/0054907 A1 | 3/2005 | Page et al. | |
| 2005/0153379 A1 | 7/2005 | Hoon et al. | |
| 2006/0238194 A1 | 10/2006 | Gleich | |
| 2007/0255122 A1 | 11/2007 | Vol et al. | |
| 2009/0123365 A1 | 5/2009 | Yang et al. | |
| 2009/0299127 A1 | 12/2009 | Rudolph et al. | |
| 2010/0049010 A1 | 2/2010 | Goldreich | |
| 2010/0204674 A1 | 8/2010 | Forbes et al. | |
| 2010/0264090 A1 | 10/2010 | Ellis et al. | |
| 2010/0322864 A1 | 12/2010 | Marcus et al. | |
| 2011/0028803 A1 | 2/2011 | Ollmar | |
| 2011/0070657 A1 | 3/2011 | Lee et al. | |
| 2011/0117028 A1 | 5/2011 | Zharov | |
| 2011/0301633 A1 | 12/2011 | Muck et al. | |
| 2012/0078068 A1 | 3/2012 | Ulmer | |
| 2012/0223705 A1 | 9/2012 | Lowery et al. | |
| 2012/0289764 A1 | 11/2012 | Murakami | |
| 2013/0144134 A1 | 6/2013 | Lee et al. | |
| 2013/0253550 A1 | 9/2013 | Beisel et al. | |
| 2013/0316355 A1 | 11/2013 | Dryga et al. | |
| 2013/0342205 A1 | 12/2013 | Prado et al. | |
| 2013/0344507 A1 | 12/2013 | Stilwell et al. | |
| 2014/0005522 A1 | 1/2014 | Zurovcik | |
| 2014/0021105 A1 | 1/2014 | Lee | |
| 2014/0170201 A1 | 6/2014 | Levy et al. | |

FOREIGN PATENT DOCUMENTS

| | | |
|---|---|---|
| WO | 2013173235 | 11/2013 |
| WO | 2013188838 A2 | 12/2013 |
| WO | 2014079505 | 5/2014 |

OTHER PUBLICATIONS

Merriam-Webster definition of Torque, Retrieved from https://www.merriam-webster.com/dictionary/torque on May 28, 2018, 8 pages.

Zhao et al., Aptamer-Linked Assay for Thrombin Using Gold Nanoparticle Amplification and Inductively Coupled Plasma-Mass Spectrometry Detection, Anal. Chem. 2009, 81, 7484-7489.

Manuel Arruebo, Monica Valladares, and Africa Gonzalez-Fernandez, Antibody-Conjugated Nanoparticles for Biomedical Applications, Journal of Nanomterials, vol. 2009 (2009), Article ID 439389, 24 pages (available at http://dx.doi.org/10.1155/2009/439389).

Shao et al., "Magnetic nanoparticles for biomedical NMR-based diagnostics," Beilstein Journal of Nanotechnology, 2010, 1, 142-154.

Liu et al., "Magnetic resonance monitoring of focused ultrasound/magnetic nanoparticle targeting delivery of therapeutic agents to the brain," PNAS Early Edition, 2010, pp. 1-6.

* cited by examiner

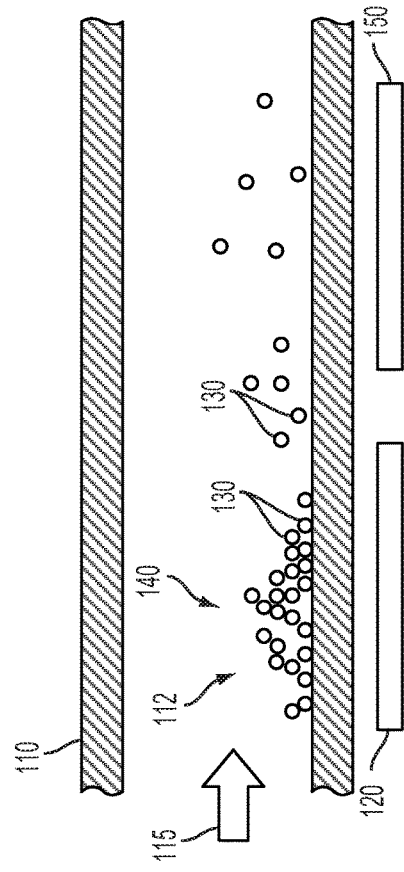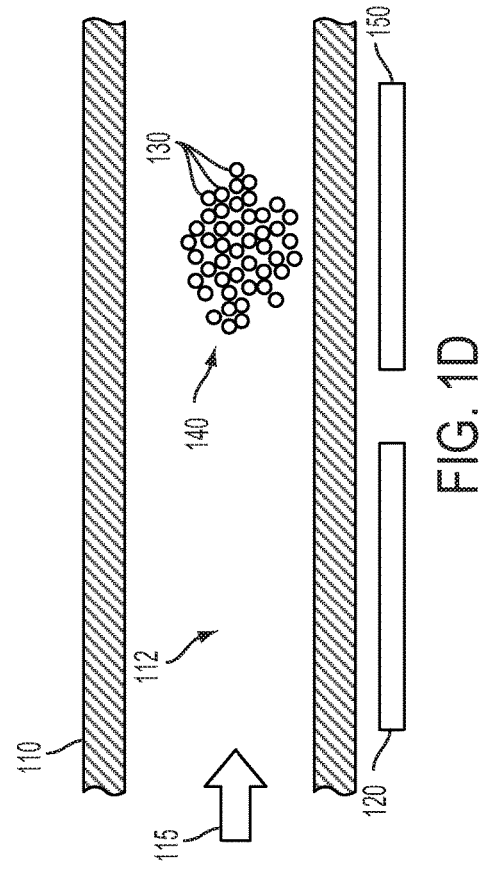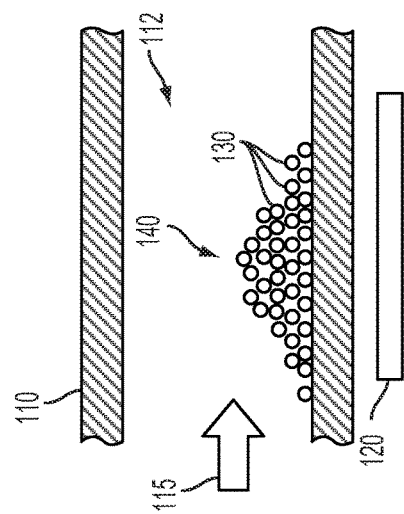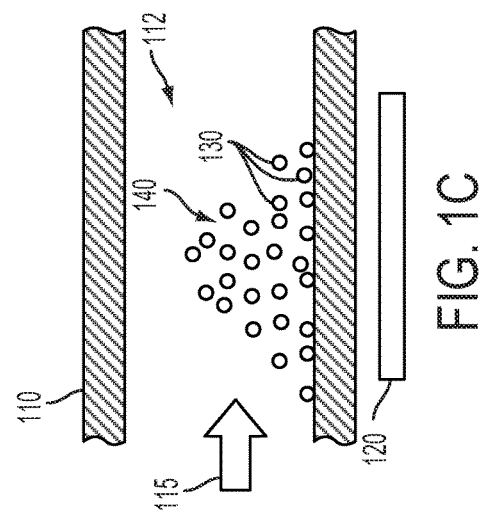

MAGNETIC SWITCHING

CROSS-REFERENCE TO RELATED APPLICATION

This application claims priority to U.S. Provisional Patent Application No. 62/053,334, filed Sep. 22, 2014, which is incorporated herein by reference.

BACKGROUND

Unless otherwise indicated herein, the materials described in this section are not prior art to the claims in this application and are not admitted to be prior art by inclusion in this section.

A number of scientific methods have been developed to detect, measure, and/or affect one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body is of scientific or medical interest. The one or more analytes could include pharmaceuticals or other substances introduced into the biological or other environment to effect some chemical or biological process. The one or more analytes could be present in living or nonliving human or animal tissue, and could be detected, measured, of affected in an in vivo, ex vivo, in vitro, or some other type of sample. The one or more analytes could include enzymes, reagents, hormones, proteins, drugs, nanoparticles, pharmaceuticals, cells or other molecules.

SUMMARY

Some embodiments of the present disclosure provide a method including: (i) positioning a device proximate to a biological environment that contains magnetic particles; (ii) operating the device, during a first period of time, to exert a first magnetic force onto the magnetic particles in the biological environment, wherein the first magnetic force is an attractive magnetic force that is sufficient to collect the magnetic particles in the biological environment proximate to the device; and (iii) operating the device, during a second period of time, to exert a second magnetic force onto the magnetic particles in the biological environment, wherein the second magnetic force is different from the first magnetic force.

Some embodiments of the present disclosure provide a system including: (i) means for positioning a device proximate to a biological environment that contains magnetic particles; (ii) means for operating the device, during a first period of time, to exert a first magnetic force onto the magnetic particles in the biological environment, wherein the first magnetic force is an attractive magnetic force that is sufficient to collect the magnetic particles in the biological environment proximate to the device; and (iii) means for operating the device, during a second period of time, to exert a second magnetic force onto the magnetic particles in the biological environment, wherein the second magnetic force is different from the first magnetic force.

Some embodiments of the present disclosure present an apparatus including a magnetic field producer, wherein the magnetic field producer is configured to be positioned proximate to an external body surface that is proximate to a portion of subsurface vasculature containing magnetic particles, wherein the magnetic field producer is configured to exert first and second magnetic forces onto the magnetic particles during respective first and second periods of time, wherein the first magnetic force is an attractive magnetic force that is sufficient to collect the magnetic particles in the portion of subsurface vasculature proximate to the device, and wherein the second magnetic force is different from the first magnetic force.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is a side cross-sectional view of magnetic particles in a portion of subsurface vasculature and a magnetic device positioned proximate to the portion of subsurface vasculature, in accordance with an example embodiment.

FIG. 1B is a side cross-sectional view of magnetic particles in a portion of subsurface vasculature and a magnetic device positioned proximate to the portion of subsurface vasculature, in accordance with an example embodiment.

FIG. 1C is a side cross-sectional view of magnetic particles in a portion of subsurface vasculature and a magnetic device positioned proximate to the portion of subsurface vasculature, in accordance with an example embodiment.

FIG. 1D is a side cross-sectional view of magnetic particles in a portion of subsurface vasculature and a magnetic device positioned proximate to the portion of subsurface vasculature, in accordance with an example embodiment.

DETAILED DESCRIPTION

Figure 2A:
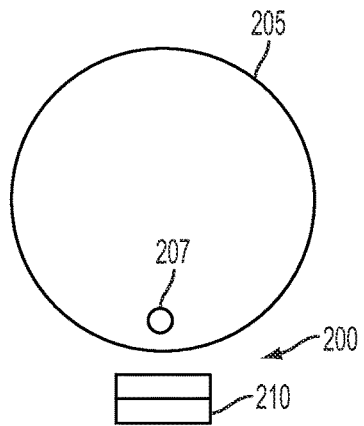
FIG. 2A is cross-sectional view of elements of an example magnetic assembly during a first period of time, while positioned near a lumen of subsurface vasculature.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Magnetic particles can be configured to selectively bind with an analyte of interest. Magnetic particles configured in this way can enable manipulation of, detection of, or other interactions with the analytes by applying magnetic forces to the magnetic particles. Additionally or alternatively, an analyte of interest could be intrinsically magnetic, or could be an engineered analyte (e.g., a pharmaceutical) that includes a magnetic property and/or that is bound to a magnetic particle and that can be introduced into an environment according to an application.

Generally, the magnetic particles may be made of and/or wholly or partially coated by an inert material, such as polystyrene, and can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. Those of skill in the art will understand a "particle" in its broadest sense and that it may take the form of any fabricated material, a molecule, cryptophane, a virus, a phage, etc. Further, a particle may be of any shape, for example, spheres, rods, non-symmetrical shapes, etc. In some examples, the particles may be magnetic and can be formed from a paramagnetic, super-paramagnetic or ferromagnetic material or any other material that responds to a magnetic field. Further, the particles can be configured to selectively bind to one or more analytes (e.g., chemicals, hormones, peptides, DNA or RNA fragments, cells).

Collection and subsequent release or other time-dependent manipulations of such magnetic particles could enable a variety of applications. The magnetic particles could be configured to selectively interact with (e.g., to bind to) one or more analytes of interest. In some embodiments, collection and other manipulations of magnetic particles could enable the detection and/or modification of one or more properties of the one or more analytes of interest. For example, magnetic particles configured to selectively interact with an analyte of interest could be collected during a first period of time. A property of the analyte of interest could be detected during or after the first period of time, and the magnetic particles could be subsequently released. Additionally or alternatively, detection of the property of the analyte of interest could include changing the magnetic field and/or magnetic force exerted on the magnetic particles during a second period of time. In some examples, the analyte of interest could have a physiological effect (e.g., could be a pharmaceutical agent) and a desired rate of action or other property or effect of the analyte of interest could be effected by controlling a magnetic field and/or magnetic force exerted on the magnetic particles.

Collection, release, modification, or other manipulations of magnetic particles could be effected by generating a time-dependent magnetic field having a specified profile in an environment containing the magnetic particles. Properties of the magnetic particles and/or the specified profile could cause motion (e.g., attractive motion toward a device producing such a magnetic field profile) of the magnetic particles, resulting in collection, release, modification, or other manipulations of the magnetic particles and/or of one or more analytes bound thereto. Magnetic forces could be applied to the magnetic particles related to applied magnetic field profiles. Magnetic forces exerted by a device could be attractive, repulsive, or have some other effect on magnetic particles in an environment. In some examples, a first magnetic force could be sufficient to collect the magnetic particles proximate to the device (e.g., to cause the magnetic particles to aggregate into a plug of magnetic particles) while a second, lesser magnetic force (e.g., a magnetic force that is substantially zero) could allow the magnetic particles to move away from the device (e.g., to release the magnetic particles). In some examples, a first magnetic force could cause the formation of a plug of magnetic particles having a first property or properties (e.g., a first rate of mass transfer and/or diffusion of an analyte of interest between regions inside the plug and regions outside of the plug) and a second magnetic force, applied to the formed plug of magnetic particles, could cause the plug to have a second property or properties (e.g., a second rate of mass flow and/or diffusion that is greater than the first rate of mass transfer and/or diffusion).

Embodiments herein relate to devices that include magnetic field producers (i.e., devices that include one or more permanent magnets, electromagnets, magnetic shims, magnetic segments, and/or other magnetic elements and that produce and/or can be operated to produce respective magnetic fields) and that are configured to generate magnetic fields (i.e., magnetic fields having a high field magnitude and/or field gradient magnitude) having specified profiles during respective periods of time such that mounting or otherwise positioning the devices proximate to a portion of subsurface vasculature or other fluid environment causes collection, release or other manipulations of magnetic particles in the subsurface vasculature or other fluid environment. These embodiments could be applied to manipulate magnetic particles in living (e.g., blood of a living human or animal) or nonliving (e.g., a sample in a container configured to enable imaging or measurement of the sample) biological environments or non-biological environments (e.g., a fluid that is part of a chemical synthesis process). In some embodiments, the devices could be wearable (e.g., configured to be worn around the wrist). Additionally or alternatively, elements of these devices could be implanted or otherwise emplaced within a human or animal body (e.g., to wholly or partially encircle a portion of subsurface vasculature or other portion of anatomy of interest). Magnetic field producers as described herein could include one or more permanent magnets, electromagnets, high-permeability poles or shims, or other magnetic or partially magnetic elements according to an application.

A magnetic field producer could include one or more permanent magnets. The one or more permanent magnets could be configured to exert high-strength magnetic forces, for example samarium-cobalt magnets, neodymium magnets, rare earth magnets, alnico magnets, ferrites, or other ferromagnetic or otherwise permanently magnetic materials. The one or more permanent magnets could have a variety of orientations (e.g., directions of the magnetic moment of the one or more dipole magnets) relative to a target environment and relative to each other. In some examples, the one or more permanent magnets include three or more dipole magnets arranged as a Halbach array. A magnetic field producer could include one or more electromagnets or could include a combination of permanent magnets and electromagnets. A magnetic field producer could be configured to generate a magnetic field having a specified profile in a portion of subsurface vasculature or other region of fluid flow that included a magnetic field gradient in a specified direction (i.e., in a direction substantially parallel to a direction of flow of fluid in the environment, e.g., along the long axis of a pipe or portion of subsurface vasculature) to generate a magnetic force on magnetic particles to oppose fluid forces on the magnetic particles due to the flow.

A magnetic field producer could be configured to produce a first magnetic field and/or to exert a first magnetic force during a first period of time and to produce a second magnetic field and/or to exert a first magnetic force during a first period of time. IN some examples, this could involve applying first and second currents and/or voltages to an electromagnet of the magnetic field producer during respective first and second periods of time. In some examples, this could involve actuating (e.g., translating, rotating, heating, or otherwise modifying the configuration of) permanent magnets, magnetic shims, or other elements of the magnetic field producer to change the configuration of such elements of the magnetic field producer from a first configuration during a first period of time to a second configuration during a second period of time. Other specified profiles of a magnetic field and changes thereof between and/or during respective periods of time in an environment of interest that contains magnetic particles (e.g., a portion of subsurface vasculature) are anticipated.

In some examples, a permanent magnet of the magnetic field producer could be translated, rotated, or otherwise actuated (e.g., by a motor, a servo, a linear actuator, or some other variety of actuator) between a first period of time and a second period of time such that respective first and second magnetic forces and/or magnetic field profiles applied to an environment and magnetic particles therein are different. Additionally or alternatively, a magnetic shim could be actuated between a first period of time and a second period of time such that respective first and second magnetic forces and/or magnetic field profiles applied to an environment and magnetic particles therein are different. Such a magnetic shim could include a sheet, pole, or other object formed from a material having a specified magnetic property (e.g., a specified high magnetic permeability) and configured to shield, focus, or otherwise alter a magnetic field produced by elements of the magnetic field producer (e.g., by one or more electromagnets, permanent magnets, or other magnetic flux producing elements). In some examples, two or more elements of a magnetic field producer could be actuated. For example, the magnetic field producer could include three or more permanent magnets whose magnetic moments are oriented such that the permanent magnets form a Halbach array having an active side and an inactive side (e.g., a side wherein a high-strength magnetic field is produced, and a side wherein substantially no magnetic field is produced, respectively). The permanent magnets of the Halbach array could be rotated between first and second periods of time such that the active side of the Halbach array is toward a target biological environment during the first period of time and away from the biological environment during the second period of time. Other methods of actuating and/or operating elements of a magnetic field producer are anticipated.

Methods, devices, and other embodiments described herein could be configured to enable a variety of applications. In some examples, magnetic particles could be configured to bind to an analyte, such that separation and/or capture of the magnetic particles could enable the detection and/or modification of one or more properties of the analyte (e.g., a concentration of the analyte). One or more properties of the analyte could be related to a medical condition of a human or animal containing the analyte. In some examples, the analyte could have a medical or other effect on the human or animal (e.g., the analyte is a toxin, the analyte is a pharmaceutical, the analyte is a cancer cell), and collecting, releasing, or otherwise manipulating magnetic particles bound to the analyte during specified periods of time could modulate or otherwise affect a medical condition of the human or animal. For example, the analyte could be a pharmaceutical, and collection and subsequent release of the magnetic particles at a specified rate (e.g., at a rate related to a specified magnetic field profile and/or magnetic force applied to the magnetic particles) could control a rate of release and/or a level of activity of the pharmaceutical in a body. In some examples, collection, release, or other manipulations of the magnetic particles could enable collection of the analyte for analysis outside the body of the human or animal. Other applications and environments containing magnetic particles are anticipated.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. ILLUSTRATIVE MAGNETIC PARTICLES AND EXERTION OF TIME-DEPENDENT MAGNETIC FORCES THEREUPON

In some examples, magnetic forces are exerted on magnetic particles disposed in a fluid environment to separate two or more of the magnetic particles. The fluid environment could include artificial environments (e.g., a fluid of an industrial process, a fluid of a chemical or pharmaceutical process) and natural environments (e.g., a lake, a river, a marsh, blood in vasculature of an animal). For example, the magnetic particles could be disposed in blood in a portion of subsurface vasculature of a human. The magnetic particles could be permanently magnetized (e.g., could be ferromagnetic) or could become magnetized when exposed to a magnetic field (e.g., could be paramagnetic) or to some other factor.

Exerting a magnetic force on such magnetic particles could include providing a magnetic field in the environment of the magnetic particles having a high magnitude of magnetic field gradient, such that permanent and/or induced magnetic moments of the magnetic particles are attracted in the direction of (i.e., experience an exerted magnetic force in the direction of) the gradient. Exerting a magnetic force on such magnetic particles could additionally or alternatively include providing a magnetic field in the environment of the magnetic particles having a high magnitude, such that magnetic moments are induced in the magnetic particles and/or permanent and/or induced magnetic moments of the magnetic particles experience a torque aligning the magnetic moments with the direction of the magnetic field. Further, exerting a magnetic force on magnetic particles could include exerting a time-dependent magnetic force; that is, a first magnetic force could be exerted on the magnetic particles during a first period of time and a second magnetic force (that could differ in magnitude, direction, or some other property) could be exerted during a second period of time.

Generally, the magnitude of a magnetic force exerted on a magnetic particle is related to the magnitude of the permanent and/or induced magnetic dipole moment of the magnetic particle. In some examples, the magnitude of the permanent and/or induced magnetic dipole moment can be related to the mass and/or volume of magnetic material included in the magnetic particle. For example, the magnitude of the induced magnetic dipole moment of a magnetic particle that includes a particle of superparamagnetic iron oxide could be related to the volume of the particle of superparamagnetic iron oxide. The magnetic particles could be artificial (e.g., functionalized polymeric shells containing and/or coating particles of superparamagnetic iron oxide), natural (e.g., particles of magnetite encapsulated in lipid bilayers in a cell), or could contain natural and artificial elements (e.g., an artificial magnetic particle onto which a variety of natural antibodies are adsorbed or otherwise attached).

Generally, the magnetic particles may be made of and/or wholly or partially coated by an inert material, such as polystyrene, and can have a diameter that is less than about 20 micrometers. In some embodiments, the magnetic particles have a diameter on the order of about 10 nm to 1 μm. In further embodiments, small particles on the order of 10-100 nm in diameter may be assembled to form larger "clusters" or "assemblies" on the order of 1-10 micrometers. Those of skill in the art will understand a "particle" in its broadest sense and that it may take the form of any fabricated material, a molecule, tryptophan, a virus, a phage, etc. Further, a magnetic particle may be of any shape, for example, spheres, rods, non-symmetrical shapes, etc. In some examples, a magnetic material of the magnetic particles can include a paramagnetic, super-paramagnetic or ferromagnetic material or any other material that responds to a magnetic field. In some examples, the magnetic particles can include a magnetic moiety. Further, the particles can be configured to selectively bind to one or more analytes (e.g., chemicals, hormones, peptides, DNA or RNA fragments, cells). In some examples, the magnetic particles could be considered to include other elements (e.g., analytes, other magnetic or non-magnetic particles) bound to the magnetic particles. For example, a 'first magnetic particle' could include a particle of magnetic material functionalized to selectively interact with an analyte, and a 'second magnetic particle' could include one or more of the 'first magnetic particles' bound to the analyte, such that the 'second magnetic particle' is a composite particle including at least one instance of the analyte. Other embodiments of magnetic particles are anticipated.

In some examples, the magnetic particles are functionalized to selectively interact with an analyte of interest. The magnetic particles can be functionalized by covalently attaching a bioreceptor designed to selectively bind or otherwise recognize a particular analyte (e.g., a clinically-relevant analyte, e.g., a cancer cell). For example, magnetic particles may be functionalized with a variety of bioreceptors, including antibodies, nucleic acids (DNA, siRNA), low molecular weight ligands (folic acid, thiamine, dimercapto-succinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), or plasmids. The functionalized magnetic particles can be introduced into a portion of subsurface vasculature of a person by injection, ingestion, inhalation, transdermal application, or in some other manner. In some examples, two or more types of magnetic particles could be configured to selectively interact with respective two or more analytes of interest. For example, first magnetic particles could be configured to selectively interact with a first analyte of interest and second magnetic particles could be configured to selectively interact with a second analyte of interest. Separation, collection, release, or other manipulations of the first and second magnetic particles by exerting magnetic forces (e.g., time-dependent magnetic forces) on the first and second magnetic particles could enable a variety of applications related to the first and second analytes of interest.

A clinically-relevant analyte could be any substance that, when present in the blood of a person or animal, or present at a particular concentration or range of concentrations, may be indicative and/or causative of an adverse medical condition. For example, the clinically-relevant analyte could be an enzyme, hormone, protein, other molecule, or even whole or partial cells. In one relevant example, certain proteins have been implicated as a partial cause of Parkinson's disease. Thus, the development of Parkinson's disease might be prevented or retarded by providing magnetic particles functionalized with a bioreceptor that will selectively bind to this target. A magnetic force may then be exerted on these bound magnetic particles, using one or more magnetic assemblies as described herein (e.g., a magnetic assembly in a wearable device mounted to an external body surface proximate to a portion of subsurface vasculature), to collect, separate, release, detect, modify, or otherwise interact with the bound protein. As a further example, the analyte could be a cancer cell. By selectively collecting and then detecting, releasing, extracting (e.g., by use of an intravenous syringe), modifying, or destroying individual cancer cells (e.g., by emitting energy toward the magnetic particles such that the magnetic particles are heated sufficiently to cause an increase in temperature of the proximate bound cancer cells), the spread of cancer may be diminished and/or quantified.

Magnetic particles and/or magnetic assemblies configured to exert time-dependent magnetic forces on such magnetic particles (and devices including such magnetic assemblies) could be configured and/or operated to provide a number of different applications. Applications could include detecting one or more properties of the magnetic particles, one or more properties of an analyte bound to or otherwise selectively interacting with the magnetic particles, collecting and/or extracting the magnetic particles and/or analytes bound to the magnetic particles, modifying and/or destroying the magnetic particles and/or analytes bound to the magnetic particles, or other applications.

Collection, separation, release, or other manipulations of magnetic particles could include exerting time-varying magnetic forces in a variety of environments to effect changes in the location, velocity, or other properties of the magnetic particles. The magnitude, direction, or other properties of magnetic forces (e.g., forces exerted by producing a magnetic field) exerted by a magnetic assembly could change over time, could be switched from one time period to the next, or could be time-varying in some other way. Correspondingly, collection, aggregation, orientation, mixing, release, detection, separation, modification, extraction, or other processes or effects on the magnetic particles, aggregates or plugs of magnetic particles, and/or analytes bound or otherwise associate with the magnetic particles could occur in a time-varying way related to changes in the magnetic force(s) exerted over time.

Magnetic particles could be collected in a portion of subsurface vasculature by exertion of magnetic forces. Collection could include exerting an attractive magnetic force (e.g., a magnetic force having an orientation toward a wall of the subsurface vasculature) on the magnetic particles. Such an attractive magnetic force could be sufficient to collect substantially all magnetic particles within the portion of subsurface vasculature (e.g., to collect substantially all magnetic particles that enter the portion of subsurface vasculature due, e.g., to blood flow) or some fraction of all of the magnetic particles within the portion of subsurface vasculature. Collection of the magnetic particles could cause the magnetic particles to associate or otherwise form into a plug, a bolus, or some other aggregated mass of magnetic particles.

A bolus, plug, or other aggregated mass of magnetic particles (referred generally herein as a plug) could have a variety of properties. A plug of magnetic particles could have a density (i.e., a spatial density of magnetic particles within the plug); further, the density of such a plug could be related to the magnitude, direction, or other properties of a magnetic force exerted on the magnetic particles making up the plug. Properties of the plug could be controlled over time by controlling and/or changing a magnetic force applied to the plug over time. For example, a rate of interaction, diffusion, and/or other mass transfer of chemicals or other elements of the environment of the plug (e.g., an analyte, a cell, a solvent) between the magnetic particles of the plug and the environment of the plug (e.g., blood in a portion of subsurface vasculature) and/or between certain magnetic particles of the plug (e.g., magnetic particles near the periphery of the plug) and certain other magnetic particles of the plug (e.g., magnetic particles near the center of the plug). Further, such plugs and/or the magnetic particles of such plugs could be configured such that the plug remains substantially intact (e.g., substantially all of the magnetic particles of the plug remain proximate to each other) in the absence of a magnetic force exerted on the plug. This can involve the magnetic particles being permanently magnetic and/or having a propensity toward aggregation, a coating of the magnetic particle being configured to encourage aggregation, a magnetic force exerted on the particles to create the plug having a sufficiently high magnitude or some other property such that the formed plug is stable, or some other operation (e.g., exertion of magnetic force(s)) and/or configuration of magnetic particles, analytes, and/or magnetic assemblies.

Exertion of magnetic forces on magnetic particles could include exerting magnetic forces such that the magnetic particles are separated. That is, exerting a force on magnetic particles could include causing and/or changing a change in displacement, velocity, and/or acceleration between the first and second magnetic particles such that a region experiences a relative increase in an amount of the first magnetic particles contained in the region and/or a relative decrease in an amount of the second magnetic particles contained in the region. For example, a magnetic force could be exerted on the first and second magnetic particles such that the first magnetic particles are collected in a region while the second magnetic particles are not attracted and/or are repelled from the region. Further, such separation could occur during a first period of time (e.g., related to the exertion of a first magnetic force on the first and/or second magnetic particles during the first period of time) and not during a second period of time (e.g., related to the exertion of a second magnetic force on the first and/or second magnetic particles during the second period of time that does not act to separate the particles). Further, a property of separation of magnetic particles (e.g., a degree of separation, a direction of separation, a selection of sets of magnetic particles to separate) could have a first value during a first period of time related to a magnetic force exerted during the first period of times and a second value during a second period of time related to a second magnetic force exerted during the second period of time.

In some examples, a magnetic assembly could be configured to exert a first magnetic force on first magnetic particles and to exert a second magnetic force on second magnetic particles such that the difference between the first and second magnetic forces is sufficient to cause separation of the first and second magnetic particles. For example, the first magnetic particles could have a first magnetic moment (e.g., related to a first characteristic size of the first magnetic particles) and the second magnetic particles could have a second magnetic moment (e.g., related to a second characteristic size of the second magnetic particles) that is different from the first magnetic moment. Additionally or alternatively, the magnetic force exerted on the magnetic particles could be substantially the same between different sets of magnetic particles (e.g., between first and second magnetic particles), but some other force (e.g., fluid drag) could be different between first and second magnetic particles such that exerting the magnetic force causes separation of the first and second magnetic particles.

Separation of first and second magnetic particles could be due additionally or alternatively to other differences between the properties of and/or environment of the first and second magnetic particles. Magnetic particles could experience a state change related to the environment (e.g., pH, temperature, presence of one or more analytes and/or other chemical or biological elements, a radiation level, an intensity, wavelength, polarization, or other property of illumination in the environment) of the magnetic particles and/or a state of the magnetic particles (e.g., a spin state, an excited energy state, a binding state, a protein folding state, a conformation, an orientation, a phosphorylation state, a methylation state, the presence of a sandwich assay protein to the magnetic particles. Additionally or alternatively, the magnetic or other differences in properties between first and second sets of magnetic particles could be intrinsic to individual instances of the first and second magnetic particles. For example, the first magnetic particles could have a first magnetic moment, coefficient of drag, cross-sectional area, or some other property, and the second magnetic particles could have a second magnetic moment, coefficient of drag, cross-sectional area, or some other property such that the first and second magnetic particles can be separated by a magnetic assembly.

To illustrate possible effects of exerting time-varying magnetic forces on magnetic particles, FIGS. 1A-1D illustrate various configurations and/or dispositions of magnetic particles 130 in a blood vessel 110. FIG. 1A illustrates the magnetic particles 130, blood vessel 110, and related elements (e.g., magnetic assemblies, detectors) during a first period of time. FIGS. 1B-1D illustrate the magnetic particles 130, blood vessel 110, and related elements (e.g., magnetic assemblies, detectors) during a second period of time, with each figure illustrating a respective disposition of magnetic particles 130 related to a respective second magnetic force exerted during a respective second period of time. That is, FIGS. 1B-1D illustrate alternative dispositions of magnetic particles 130 related to alternative exerted second magnetic forces, following the configuration illustrated in FIG. 1A.

FIG. 1A illustrates a lumen 112 of a blood vessel (i.e., a portion of subsurface vasculature) 110 during a first period of time. Blood in the lumen 112 is flowing, as indicated by the arrow 115. Magnetic particles 130 are located in the lumen 112 of the blood vessel 110 and have aggregated into a plug 140. A magnetic assembly 120 (e.g., a device including permanent magnets, magnetic shims, electromagnets, actuators, and/or other magnetic components) is disposed outside of the blood vessel 110 (e.g., part of a device positioned proximate to an external body surface proximate to the blood vessel 110) and is configured and/or operated during the first period of time to exert a first magnetic force on the magnetic particles 130 such that the magnetic particles 130 are collected and aggregate into the plug 140. The magnetic assembly 120 is configured to exert a time-varying magnetic force (e.g., to produce a magnetic field in the lumen 112 of the blood vessel 110) and is configured and/or operated during the first period of time to exert the first magnetic force.

The magnetic assembly 120 could exert a second magnetic force during a second period of time such that the magnetic particles 130 are released (e.g., released form the plug 140) during the second period of time. For example, the second magnetic force could be such that the magnetic particles move away from the magnetic assembly 120 during the second period of time at a rate that is related to the second magnetic force. FIG. 1B illustrates the lumen 112 of the blood vessel (i.e., a portion of subsurface vasculature) 110 during a second period of time. The magnetic assembly 120 is configured and/or operated during the second period of time to exert a second magnetic force on the magnetic particles 130 such that some of the magnetic particles 130 are released from the proximity of the magnetic assembly 120 (e.g., released from the plug 140) and flow within the lumen 112 to a downstream location. FIG. 1B additionally illustrates a sensor 150 that is disposed proximate to the downstream location and that could be used, e.g., to detect a property of the magnetic particles 130 (and/or of an analyte bound or otherwise attached thereto) that are released and that flow to the downstream location during the second period of time.

A second magnetic force could be exerted during a second period of time such that a property of the plug 140 (e.g., a density, a rate of interaction, diffusion, and/or other mass transfer between the collected magnetic particles and blood in the lumen 112) had a different value during the second period of time relative to the first period of time. FIG. 1C illustrates the lumen 112 of the blood vessel (i.e., a portion of subsurface vasculature) 110 during a second period of time. The magnetic assembly 120 is configured and/or operated during the second period of time to exert a second magnetic force on the magnetic particles 130 such that the magnetic particles 130 within the plug 140 are less densely packed and allow more diffusion or other mass transfer between regions within the plug 140 and blood in the lumen 112. This could allow the movement of an analyte within blood in the lumen 112 to move (e.g., by diffusion) into the plug 140 and to selectively interact with (e.g., bind to) the magnetic particles. Additionally or alternatively, this could allow analytes bound to magnetic particles 130 of the plug 140 or otherwise contained within the plug 140 during the first period of time to move (e.g., by diffusion) out of the plug 140 and into blood of the lumen 112.

A second magnetic force could be exerted during a second period of time such that the plug 140 is released (i.e., such that the magnetic particles 130 are released while remaining proximate to each other as an aggregated mass) during the second period of time. For example, the second magnetic force could be such that the plug 140 moves away from the magnetic assembly 120 during the second period of time. FIG. 1D illustrates the lumen 112 of the blood vessel (i.e., a portion of subsurface vasculature) 110 during a second period of time. The magnetic assembly 120 is configured and/or operated during the second period of time to exert a second magnetic force on the magnetic particles 130 such that substantially all of the magnetic particles 130 forming the plug 140 are released from the proximity of the magnetic assembly 120 and remain substantially proximate to each other (i.e., remain substantially aggregated as part of the plug 140) as they flow within the lumen 112 to a downstream location. FIG. 1D additionally illustrates a sensor 150 that is disposed proximate to the downstream location and that could be used, e.g., to detect a property of the magnetic particles 130, the plug 140, and/or of an analyte bound or otherwise attached thereto that flow to the downstream location during the second period of time.

In some examples, magnetic particles could be configured to bind to an analyte of interest, and a magnetic assembly could be configured to collect, release, separate, or otherwise manipulate the magnetic particles to enable the detection, extraction, modification, or other manipulation of the analyte. For example, the magnetic assembly could be configured to produce a time-dependent magnetic field in the portion of subsurface vasculature such that magnetic particles experience a first magnetic force during a first period of time that is sufficient to collect the magnetic particles (and any instances of the analyte bound or otherwise attached thereto) in the portion of subsurface vasculature proximate to the magnetic assembly. The magnetic assembly could then be operated such that the magnetic particles experience a second magnetic force during a second period of time to allow some application.

For example, the second magnetic force could be such that the magnetic particles (and/or an aggregate or plug thereof) are released from the portion of subsurface vasculature (e.g., as in the scenarios described in relation to FIGS. 1B and 1D). This could allow extraction of the analyte bound to the magnetic particles (e.g., by a needle penetrating into a portion of subsurface vasculature downstream from the region wherein the magnetic particles are collected during the first period of time) or some other application. In some examples, the second magnetic force could be such that the magnetic particles (and the analyte (e.g., a pharmaceutical) bound thereto) are released from the portion of subsurface vasculature at a specified rate (e.g., as in the scenarios described in relation to FIG. 1B). Magnetically controlling such a specified rate of release could be used to control a rate of activity of the analyte, e.g., to control a rate of overall physiological activity of a pharmaceutical bound to the magnetic particles within a body of a human or animal.

In some examples, the second magnetic force could be such that a rate of interaction, diffusion, and/or other mass transfer of the analyte between the collected magnetic particles and blood in the portion of subsurface vasculature is different during the second period of time relative to the first period of time. That is, the second magnetic force, relative to the first magnetic force, could be such that a separation distance, rate of mixing, or some other property of the aggregation of the magnetic particles was different during the second period of time (e.g., as in the scenarios described in relation to FIG. 1C). For example, a separation distance between collected magnetic particles could be greater during the second period of time, such that analyte present in blood of the portion of subsurface vasculature is able to interact with the magnetic particles (e.g., to be bound to the magnetic particles, and/or to magnetic particles within an aggregate or plug of collected magnetic particles) to a greater degree during the second period of time than during the first period of time. Additionally or alternatively, instances of the analyte already bound or otherwise attached to the magnetic particles and/or disposed within an aggregate could be able to diffuse out into the blood of the portion of subsurface vasculature to a greater degree during the second period of time than during the first period of time. Magnetically controlling such a rate of interaction, diffusion, and/or other mass transfer of the analyte could be used to control a rate of activity of the analyte, e.g., to control a rate of overall physiological activity of a pharmaceutical bound to the magnetic particles within a body of a human or animal.

In some embodiments, a detector could be disposed proximate to a magnetic assembly that is configured to collect, release, aggregate, separate, or otherwise manipulate the magnetic particles by exerting time-dependent magnetic forces, and the detector could detect one or more properties of an analyte bound to some or all of the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the separated and/or collected magnetic particles sufficient to alter one or more properties of the analyte (e.g., to destroy, denature, heat, change a conformation state of, other otherwise modify the analyte). In some examples, collection and release of an analyte bound to magnetic particles by a magnetic assembly could enable the extraction of the analyte and magnetic particles (e.g., using a hypodermic needle).

In some examples, collection and/or aggregation of sufficient amounts of the analyte and/or magnetic particles bound thereto for detection (e.g., to allow for the detection of an optical, magnetic, or other signal related to the analyte having an amplitude, a signal-to-noise-ratio, or some other property beyond a specified threshold level) could include the exertion of a magnetic force and/or production of a magnetic field that is incompatible with detection of a property of interest of the analyte.

In some examples, detection could involve detection of magnetic resonance properties of the analyte and/or magnetic particles in a magnetic field that has a gradient that is substantially zero. In such examples, a magnetic assembly could be operated to exert a first magnetic force (e.g., a magnetic force having a large, non-zero magnitude of magnetic field gradient) during a first period of time to collect magnetic particles and an analyte bound thereto. The magnetic assembly could then, during a second period of time, be operated to exert a second magnetic force that is lower than the first magnetic force and that allows the collected magnetic particles (and/or an aggregate or plug composes of such) to flow downstream to a region having a magnetic field that has a gradient that is substantially zero, allowing detection of magnetic resonance properties of the analyte and/or magnetic particles (e.g., similar to the scenarios depicted in relation to FIGS. 1B and 1D). Additionally or alternatively, the magnetic assembly could be operated during the second period of time to produce such a magnetic field that has a gradient that is substantially zero, such that the of magnetic resonance properties of the analyte and/or magnetic particles could be detected while the magnetic particles are proximate to the magnetic assembly.

In some examples, the magnetic assembly could be operated to exert a first magnetic force during a first period of time to collect the magnetic particles and an analyte bound thereto. The magnetic assembly could then, during a second period of time, be operated to exert a second magnetic force that is lower than the first magnetic force and that allows the collected magnetic particles (and/or an aggregate or plug composes of such) to flow downstream to a region that can be interrogated by a detector such that a property of interest of the magnetic particles and/or analyte can be detected (e.g., similar to the scenarios depicted in relation to FIGS. 1B and 1D). Other operations, configurations, and applications of magnetic assemblies and magnetic particles to detect, modify, or otherwise interact with an analyte are anticipated.

It is also anticipated that time-dependent magnetic forces exerted on magnetic particles could have one or more properties (e.g., magnitude, direction) that vary over time in a continuous manner according to an application. For example, a magnetic assembly could be operated to exert a continuously varying magnetic force on magnetic particles to control a rate of aggregation of the magnetic particles, to control a rate of release of the magnetic particles, to control a rate of mass transfer of an analyte toward/away from the magnetic particles, or to control some other property or properties of the magnetic particles, of an aggregate and/or plug of such particles, the analyte, or some other aspect of the environment of the magnetic particles. Such continuous variation of a magnetic force exerted by a magnetic assembly (e.g., a magnetic assembly as described herein) could be controlled according to a specified profile of magnetic force over time, a detected property of the magnetic particles and/or the environment thereof (e.g., a detected rate of release of the magnetic particles, a detected rate of physiological activity of an analyte to which the magnetic particles are configured to bind), or according to some other consideration or application.

The terms "binding", "bound", and related terms used herein are to be understood in their broadest sense to include any interaction between the receptor and the target or another functionalized particle such that the interaction allows the target to be modified or destroyed by energy emitted from a wearable device.

III. EXAMPLE MAGNETIC ASSEMBLIES

In some applications, it can be desirable to produce magnetic fields having high magnitude, high magnitude of field gradient, a specified field profile, or other properties using a small device and using minimal power. For example, an application could include a wearable device configured to be powered by a battery disposed in the device and to attract magnetic particles in the body of a wearer of a device. Such magnetic fields could be produced by magnetic assemblies that include magnetic elements (i.e., permanent magnets, electromagnets, and other components that have and/or can be operated to have a magnetic dipole moment), paramagnetic materials, flux-focusing and/or shielding shims or poles, or other elements. A class of such magnetic elements includes unpowered elements, e.g., permanent magnets and other magnetic materials capable of generating a magnetic field having a desired profile, magnitude, or other property while requiring significantly no applied power. Further, such produced magnetic fields and/or exerted magnetic forces related thereto could be time-dependent; that is, a magnetic assembly could be operated and/or configured to produce a first magnetic field and/or to exert a first magnetic force during a first period of time and to produce a second magnetic field and/or to exert a second magnetic force during a second period of time.

Operation and/or configuration of a magnetic assembly to exert time-dependent magnetic forces could include operating elements of the magnetic assembly in a variety of ways. In some examples, a magnetic assembly could include an electromagnet, and operating the magnetic assembly to exert time-dependent magnetic forces could include applying time-dependent currents and/or voltages to the electromagnet related to the time-dependent magnetic forces. Operating a magnetic assembly to exert time-dependent magnetic forces could include mechanically controlling, in a time-dependent manner, the location, orientation, or other properties of one or more elements of the magnetic assembly (e.g., of one or more electromagnets, permanent magnets, magnetic shims, or other elements). For example, the configuration of one or more magnetic elements (e.g., permanent magnets, magnetic shims, electromagnets) could be controlled by one or more actuators. For example, a permanent magnet could be mounted to an armature or other mechanism that is driven by an actuator (e.g., a servo) such that the actuator could be operated to rotate the permanent magnet and thus to rotate the direction of the magnetic moment of the magnet.

To illustrate possible configurations and/or operations of a magnetic assembly to exert time-varying magnetic forces on magnetic particles by mechanically controlling one or more properties of one or more elements of the magnetic assembly, FIGS. 2A-2E illustrate cross-sectional views of various configurations and/or dispositions of an example magnetic-flux-producing element 210 (e.g., a permanent magnet) of a magnetic assembly 200 that is positioned proximate to a portion of subsurface vasculature 207 that contains magnetic particles and that is located within an arm 205. FIG. 2A illustrates the portion of subsurface vasculature 207, arm 205, and magnetic-flux-producing element 210 of the magnetic assembly 200 during a first period of time. FIGS. 2B-2E illustrate the portion of subsurface vasculature 207, arm 205, and magnetic-flux-producing element 210 of the magnetic assembly 200 during a second period of time, with each figure illustrating a respective disposition of the magnetic-flux-producing element 210 related to a respective second magnetic force exerted during a respective second period of time. That is, FIGS. 2B-2E illustrate alternative dispositions of the magnetic-flux-producing element 210 related to alternative exerted second magnetic forces, following the configuration illustrated in FIG. 2A.

Note that the magnetic-flux-producing element 210 illustrated in FIGS. 2A-2E could be a single magnetic dipole element (e.g., a single permanent magnet, a single electromagnet). Alternatively, the magnetic-flux-producing element 210 could represent a plurality of magnetic elements (e.g., a combination of permanent magnets, electromagnets, or other magnetic-flux-producing elements) or other components of a magnetic assembly (e.g., magnetic shims, spacers, housings, actuators).

FIG. 2A illustrates a portion of subsurface vasculature 207 within an arm 205 during a first period of time. A magnetic assembly 210 (e.g., a device including permanent magnets, magnetic shims, electromagnets, actuators, or other magnetic components) includes a magnetic-flux-producing element 210 and is disposed outside of the arm 205 proximate to the portion of subsurface vasculature 207. The magnetic assembly 210 is configured and/or operated during the first period of time to exert a first magnetic force on magnetic particles disposed in the portion of subsurface vasculature 207. The magnetic assembly 210 is configured to exert a time-dependent magnetic force (e.g., to produce a time-dependent magnetic field in the portion of subsurface vasculature 207) and is configured and/or operated during the first period of time to exert the first magnetic force.

Figure 2B:
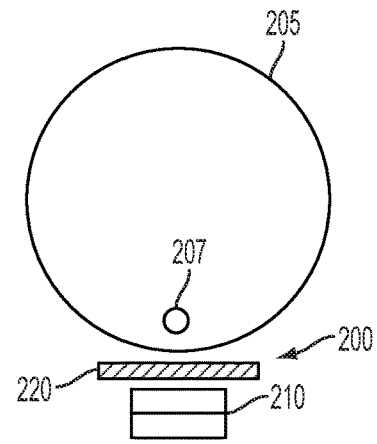
FIG. 2B is cross-sectional view of the elements of the example magnetic assembly of FIG. 2A during a second period of time.

A magnetic shim (e.g., a material having a specified high magnetic permeability) of the magnetic assembly 200 could be translated, oriented, or otherwise actuated, between the first and second periods of time, such that the magnetic assembly 200 exerts a second magnetic force on magnetic particles disposed in the portion of subsurface vasculature 207 during the second period of time, where the second magnetic force is different than the first magnetic force. FIG. 2B illustrates the portion of subsurface vasculature 207 within the arm 205 during a second period of time. A magnetic shim 220 is interposed between the arm 205 and the magnetic-flux-producing element 210 such that a magnetic field produced by the magnetic assembly within the portion of subsurface vasculature 207 (i.e., an amount of magnetic flux within the portion of subsurface vasculature 207) is reduced. Thus, the magnetic assembly 200 exerts a second magnetic force on magnetic particles disposed in the portion of subsurface vasculature 207 that is less than the first magnetic force. Alternatively, a magnetic shim could act to focus the magnetic flux produced by the magnetic-flux-producing element 210 on the portion of subsurface vasculature 207 (e.g., the magnetic shim could have a narrowing geometry toward the portion of subsurface vasculature 207) such that the second exerted magnetic force is greater than the first exerted magnetic force. Alternative geometries of and compositions of magnetic shims are anticipated.

Figure 2C:
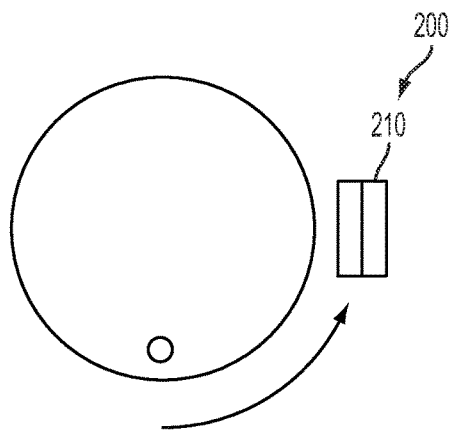
FIG. 2C is cross-sectional view of the elements of the example magnetic assembly of FIG. 2A during a second period of time.
Figure 2D:
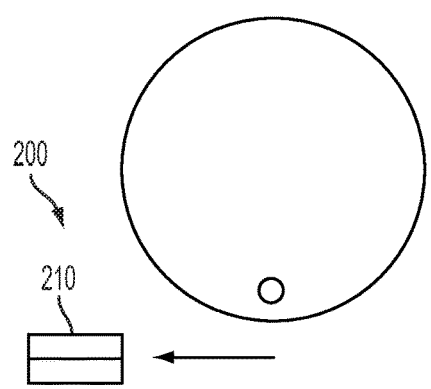
FIG. 2D is cross-sectional view of the elements of the example magnetic assembly of FIG. 2A during a second period of time.

The magnetic-flux-producing element 210 of the magnetic assembly 200 could be translated, oriented, or otherwise actuated, between the first and second periods of time, such that the magnetic assembly 200 exerts a second magnetic force on magnetic particles disposed in the portion of subsurface vasculature 207 during the second period of time, where the second magnetic force is different than the first magnetic force. FIGS. 2C and 2D illustrate the portion of subsurface vasculature 207 within the arm 205 during alternative second periods of time. The magnetic-flux-producing element 210 is translated and rotated around the arm 205 and translated laterally away from the arm 205 in FIGS. 2C and 2D, respectively, such that a magnetic field produced by the magnetic assembly 200 within the portion of subsurface vasculature 207 (i.e., an amount of magnetic flux within the portion of subsurface vasculature 207) is reduced. Thus, the magnetic assembly 200 exerts a second magnetic force on magnetic particles disposed in the portion of subsurface vasculature 207 that is less than the first magnetic force.

Figure 2E:
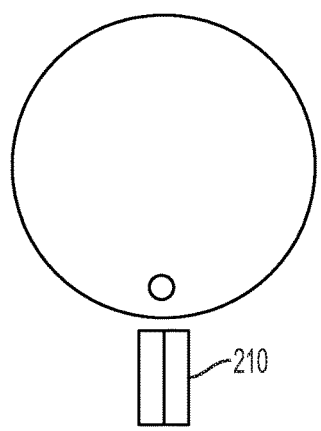
FIG. 2E is cross-sectional view of the elements of the example magnetic assembly of FIG. 2A during a second period of time.

A magnetic moment of the magnetic-flux-producing element 210 of the magnetic assembly 200 could be rotated (e.g., by rotating the magnetic-flux-producing element 210 using a motor or other actuator), between the first and second periods of time, such that the magnetic assembly 200 exerts a second magnetic force on magnetic particles disposed in the portion of subsurface vasculature 207 during the second period of time, where the second magnetic force is different than the first magnetic force. FIG. 2E illustrates the portion of subsurface vasculature 207 within the arm 205 during a second period of time. The magnetic-flux-producing element 210 is rotated (i.e., the orientation of the magnetic moment of the magnetic-flux-producing element 210 is changed) such that a magnetic field produced by the magnetic assembly 200 within the portion of subsurface vasculature 207 (i.e., an amount of magnetic flux within the portion of subsurface vasculature 207) is changed. Thus, the magnetic assembly 200 exerts a second magnetic force on magnetic particles disposed in the portion of subsurface vasculature 207 that is different from the first magnetic force.

In some examples, multiple elements of a magnetic assembly could be actuated between a first and second period of time such that the magnetic assembly exerts different respective first and second magnetic forces. For example, a magnetic assembly could include a plurality of magnetic elements configured as a Halbach array. Such a Halbach array could have a first side toward an environment of interest (e.g., toward a portion of subsurface vasculature containing magnetic particles) and a second side away from the environment of interest. During a first period of time, the magnetic elements of the Halbach array could be produce a large magnetic field on the first side of the array and a small magnetic field on the second side. The magnetic moments of one or more of the magnetic elements of the array could be rotated by specified amounts between the first period of time and a second period of time such that, during the second period of time, the Halbach array produces a small magnetic field on the first side of the array and a large magnetic field on the second side. Thus, the magnetic assembly could exert a first magnetic force during the first period of time and a second magnetic force during the second period of time.

Figure 3A:
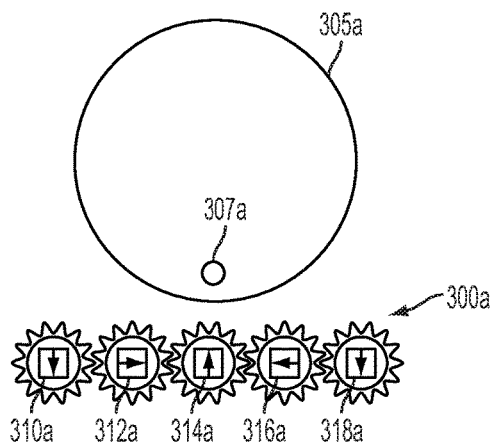
FIG. 3A is cross-sectional view of elements of an example magnetic assembly during a first period of time, while positioned near a lumen of subsurface vasculature.

FIG. 3A illustrates a portion of subsurface vasculature 307a within an arm 305a during a first period of time. A magnetic assembly 300a (e.g., a device including permanent magnets, magnetic shims, electromagnets, actuators, or other magnetic components) includes a plurality of magnetic elements 310a, 312a, 314a, 316a, 318a having respective magnetic moments and arranged as a Halbach array. The magnetic assembly 300a is disposed outside of the arm 305a proximate to the portion of subsurface vasculature 307a. The magnetic assembly 300a is configured during the first period of time to exert a first magnetic force on magnetic particles disposed in the portion of subsurface vasculature 307a. The magnetic assembly 300a is configured to exert a time-dependent magnetic force (e.g., to produce a time-dependent magnetic field in the portion of subsurface vasculature 307a) and is configured and/or operated during the first period of time to exert the first magnetic force.

Figure 3B:
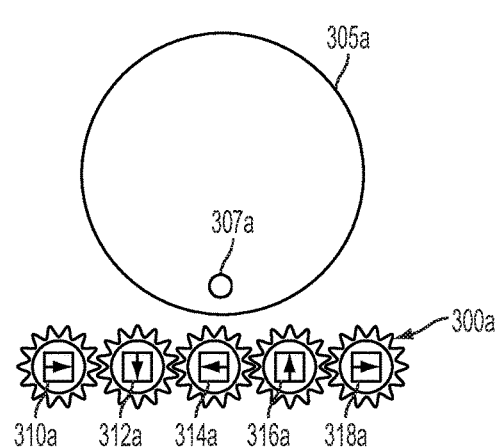
FIG. 3B is cross-sectional view of the elements of the example magnetic assembly of FIG. 3A during a second period of time.

The magnetic elements 310a, 312a, 314a, 316a, 318a are individually geared, as illustrated in FIG. 3A, such that their respective magnetic moments can be rotated together, and further, such that the rotations of neighboring magnetic elements are opposite (e.g., a clockwise rotation of the magnetic moment of 310a would be accompanied, due to the gearing, with a counter-clockwise rotation of the magnetic moment of 312a). FIG. 3B illustrates the portion of subsurface vasculature 307a within the arm 305a during a second period of time. The magnetic elements 310a, 312a, 314a, 316a, 318a are rotated 90 degrees relative to their configuration in FIG. 3A. Thus, the magnetic assembly 300a exerts a second magnetic force on magnetic particles disposed in the portion of subsurface vasculature 307a that is less than the first magnetic force.

Figure 3C:
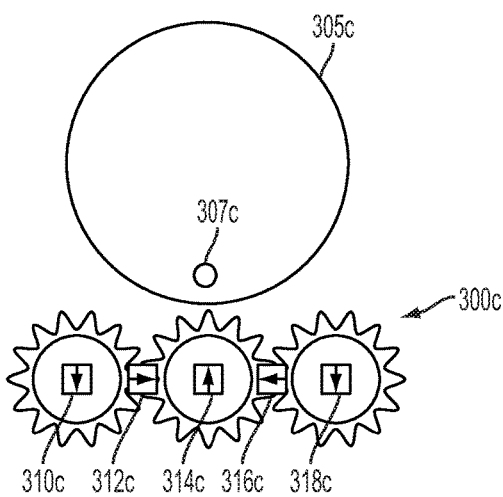
FIG. 3C is cross-sectional view of elements of an example magnetic assembly during a first period of time, while positioned near a lumen of subsurface vasculature.

FIG. 3C illustrates a portion of subsurface vasculature 307c within an arm 305c during a first period of time. A magnetic assembly 300c (e.g., a device including permanent magnets, magnetic shims, electromagnets, actuators, or other magnetic components) includes a plurality of magnetic elements 310c, 312c, 314c, 316c, 318c having respective magnetic moments and arranged as a Halbach array. The magnetic assembly 300c is disposed outside of the arm 305c proximate to the portion of subsurface vasculature 307c. The magnetic assembly 300c is configured during the first period of time to exert a first magnetic force on magnetic particles disposed in the portion of subsurface vasculature 307c. The magnetic assembly 300c is configured to exert a time-dependent magnetic force (e.g., to produce a time-dependent magnetic field in the portion of subsurface vasculature 307c) and is configured and/or operated during the first period of time to exert the first magnetic force.

Figure 3D:
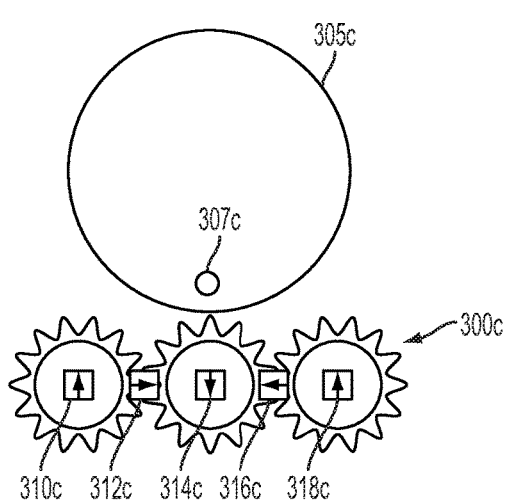
FIG. 3D is cross-sectional view of the elements of the example magnetic assembly of FIG. 3C during a second period of time.

The magnetic elements 310c, 314c, 318c are individually geared, as illustrated in FIG. 3C, such that their respective magnetic moments can be rotated together, and further, such that the rotations of alternate magnetic elements are opposite (e.g., a clockwise rotation of the magnetic moment of 310c would be accompanied, due to the gearing, with a counterclockwise rotation of the magnetic moment of 314c). Magnetic elements 312c and 316c are configured to remain fixed as magnetic elements 310c, 314c, and 316c rotate. FIG. 3D illustrates the portion of subsurface vasculature 307c within the arm 305c during a second period of time. The magnetic elements 310c, 314c, 318c are rotated 180 degrees relative to their configuration in FIG. 3C. Thus, the magnetic assembly 300c exerts a second magnetic force on magnetic particles disposed in the portion of subsurface vasculature 307c that is less than the first magnetic force.

The magnetic assemblies 300a, 300c of FIGS. 3A-3D are intended as non-limiting examples. Magnetic assemblies could fewer or more magnetic elements arranged as a Halbach array or according to some other configuration. Further, such magnetic elements could be geared or otherwise commonly actuated in a manner similar to that shown, or according to some other application.

Other configurations and/or operations of a magnetic assembly and/or elements or sub-assemblies thereof to control, over time, magnitude, direction, or other properties of a magnetic force exerted by the magnetic assembly are anticipated. For example, heat could be applied to a permanent magnet to reduce the amount of magnetic flux produced by the permanent magnet or to change some other property of the permanent magnet (e.g., to change a coercivity, a property of hysteresis, a permeability, a saturation). In another example, a magnetic and/or electric field could be applied to a material (e.g., a magneto- and/or electrostrictive material) to change a magnetic property of the material. The direction and/or amount of magnetization of permanent-, anti-ferro-, ferri-, ferro-, para-, superpara-, or otherwise-magnetic material could be controlled by the application of magnetic field, e.g., by an electromagnet.

Magnetic assemblies could include a variety of magnetic or other elements configured in a variety of ways and further configured to be operated and/or re-configured to exert a time-dependent magnetic force (e.g., on magnetic particles in a portion of subsurface vasculature. FIGS. 4A-4D, 5A-5E, 6A, 6B, 7, and 8A-8D illustrate a variety of configurations of magnetic and other elements of magnetic assemblies. Such magnetic assemblies as described in relation to these figures could be configured and or operated as described herein to exert time-dependent magnetic forces. That is, any individual element (e.g., an individual permanent magnet, an individual magnetic shim, and individual electromagnet) or combination of elements of such magnetic assemblies could be translated, rotated, or otherwise operated or manipulated as described herein such that the magnetic assembly exerted a time-dependent magnetic force related to such translation, rotation, or other operation of manipulation.

Such magnetic assemblies could include one or more magnetic elements, with each magnetic element of the one or more magnetic elements having a respective magnetic moment that is oriented relative to an environment of interest (e.g., a portion of subsurface vasculature of a user of a device that includes the one or more magnetic elements) to enable some application (e.g., the exertion of a magnetic force to enable collection, release, separation, or some other manipulation of one or more magnetic particles in the portion of subsurface vasculature). Magnetic assemblies could additionally or alternatively include magnetic shims or poles (e.g., materials having high magnetic permeability or some other specified magnetic property) configured to focus magnetic flux toward a specified region of an environment and/or shield a specified region of an environment from magnetic flux.

Additionally or alternatively, magnetic flux could be produced by electromagnets or other powered elements. In embodiments described herein, a particular permanent magnet may be replaced with an electromagnet such that, when a specified current is applied to the electromagnet, the electromagnet could produce a pattern of magnetic flux substantially the same as a pattern of magnetic flux produced by the particular permanent magnet.

Figure 4A:
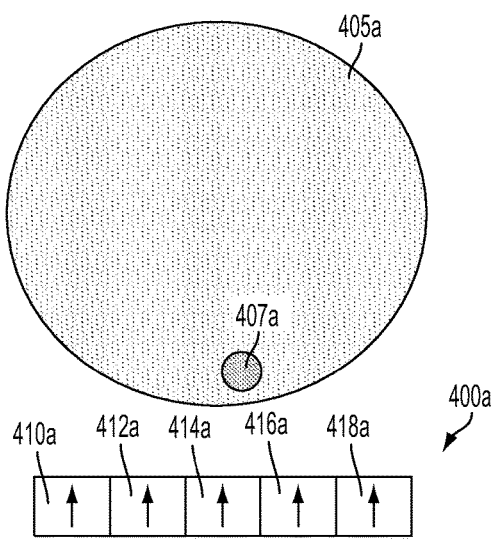
FIG. 4A is cross-sectional view of an example magnetic assembly, while positioned near a lumen of subsurface vasculature.

FIG. 4A illustrates a schematic diagram of an example magnetic assembly 400a comprising a plurality of magnetic elements 410a, 412a, 414a, 416a, 418a having respective magnetic moments (arrows). The magnetic assembly 400a is positioned proximate to a portion of subsurface vasculature 407a within a body of a human 405a. The magnetic assembly 400a could be part of a wearable device and the wearable device could further include a mount configured to mount the wearable device to an external body surface of the body of the human 405a proximate to the portion of subsurface vasculature 407a. The permanent magnets 410a, 412a, 414a, 416a, 418a of the magnetic assembly 400a can be configured and/or operated to exert a time-dependent magnetic force on magnetic particles in the portion of subsurface vasculature 407a.

Magnetic elements of a magnetic assembly could have magnetic moments oriented in substantially the same direction (as illustrated in the example of FIG. 4A) or could have a number of orientations relative to each other and/or to an environment of interest. In some examples, the orientations of the magnetic moments could be specified to increase one or more properties of a generated magnetic field (e.g., a field magnitude, a magnitude of a field gradient) in a first region and/or to reduce one or more properties of the generated magnetic field in a second region. For example, the magnetic moments of three or more magnetic elements in a magnetic assembly could be arranged as a Halbach array to increase the magnitude of the magnetic field on one side of the magnetic assembly and to decrease the magnitude of the magnetic field on an opposite side of the magnetic assembly.

Figure 4B:
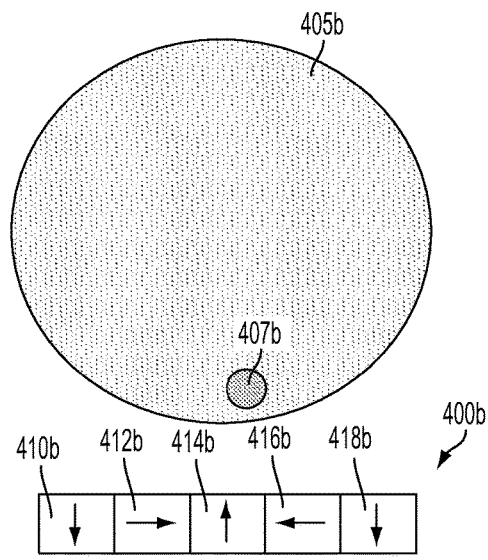
FIG. 4B is cross-sectional view of an example magnetic assembly, while positioned near a lumen of subsurface vasculature.

FIG. 4B illustrates a schematic diagram of an example magnetic assembly 400b comprising a plurality of magnetic elements 410b, 412b, 414b, 416b, 418b having respective magnetic moments (arrows) oriented such that the magnetic assembly forms a Halbach array. The magnetic assembly 400b is positioned proximate to a portion of subsurface vasculature 407b within a body of a human 405b. The magnetic assembly 400b could be part of a wearable device and the wearable device could further include a mount configured to mount the wearable device to an external body surface of the body of the human 405b proximate to the portion of subsurface vasculature 407b. The magnetic elements 410b, 412b, 414b, 416b, 418b of the magnetic assembly 400b can be configured and/or operated to exert a time-dependent magnetic force on magnetic particles in the portion of subsurface vasculature 407b. The magnetic elements 410b, 412b, 414b, 416b, 418b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated.

In some examples, the magnetic assembly could wholly or partially enclose an environment (e.g., an aspect of a body of a wearer, e.g., a wrist). That is, a magnetic assembly and/or a wearable or other device including a magnetic assembly could have a concave surface configured to at least partially enclose a corresponding convex surface of an environment of interest (e.g., the magnetic assembly could have a concave surface configured to at least partially enclose a convex shape of an external body surface of a human or other target of the magnetic assembly). Further, one or more of a plurality of permanent magnets (or other flux-producing elements) of the magnetic assembly could be disposed on the concave surface of the magnetic assembly.

Figure 4C:
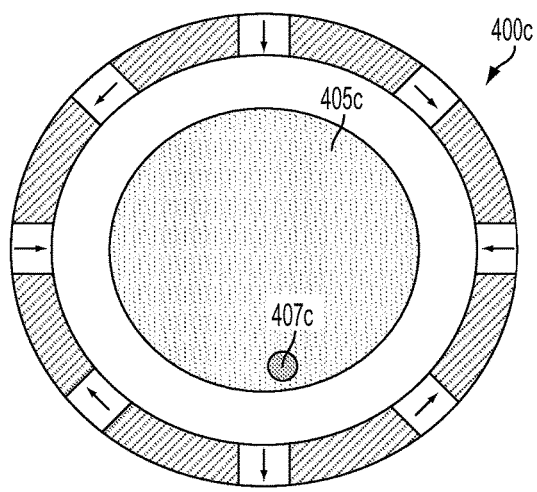
FIG. 4C is cross-sectional view of an example magnetic assembly, while positioned near a lumen of subsurface vasculature.
Figure 4D:
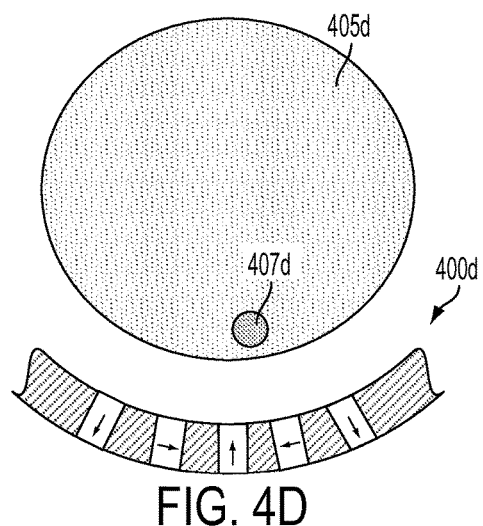
FIG. 4D is cross-sectional view of an example magnetic assembly, while positioned near a lumen of subsurface vasculature.

FIGS. 4C and 4D illustrate schematic diagrams of example magnetic assemblies 400c, 400d comprising respective pluralities of magnetic elements having respective magnetic moments (arrows) oriented such that the magnetic assemblies 400c, 400d form respective configurations of Halbach arrays. The magnetic assemblies 400c, 400d are positioned proximate to respective portions of subsurface vasculature 407c, 407d within respective bodies of respective humans 405c, 405d. The magnetic assemblies 400c, 400d could be part of respective wearable devices and the wearable devices could further include mounts configured to mount the wearable devices to respective external body surfaces of the bodies of the respective humans 405c, 405d proximate to the respective portions of subsurface vasculature 407c, 407d. The magnetic elements of the magnetic assemblies 400c, 400d can be configured and/or operated to exert time-dependent magnetic forces on magnetic particles in respective portions of subsurface vasculature 407c, 407d.

Magnetic assemblies can include magnetic poles (also called magnetic shims) configured to focus, block, or otherwise modify a pattern of magnetic flux and/or a magnetic field profile generated by one or more magnetic elements. The magnetic poles can have a variety of specified geometries and be composed of a variety of materials according to a variety of applications. The magnetic poles could be composed of materials having a specified magnetic property (e.g., permeability, reluctance, susceptibility, coercivity, remanence, saturation level). For example, the magnetic poles could be composed of one or more materials having a high magnetic permeability, e.g., mu-metal, iron, steel, metglas, Permalloy, ferrite, or other materials.

Figure 5A:
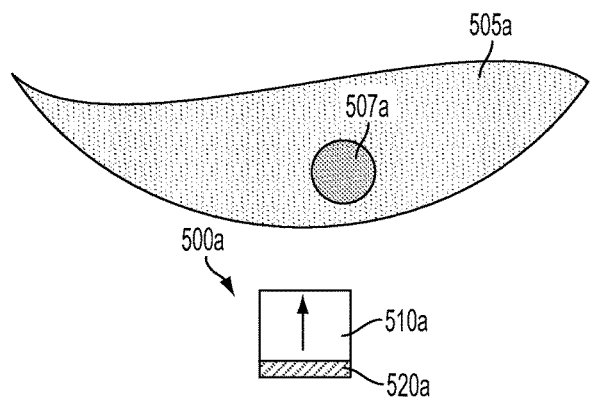
FIG. 5A is cross-sectional view of an example magnetic assembly, while positioned near a lumen of subsurface vasculature.

FIG. 5A illustrates a schematic diagram of an example magnetic assembly 500a comprising a magnetic element 510a having a magnetic moment (arrow) and a magnetic pole 520a comprising a high-permeability material. The magnetic assembly 500a is positioned proximate to a portion of subsurface vasculature 507a within a body of a human 505a. The magnetic pole 520a comprises a layer of the high-permeability material disposed on a side of the magnetic assembly 500a opposite the human body 505a. The magnetic assembly 500a could be part of a wearable device and the wearable device could further include a mount configured to mount the wearable device to an external body surface of the body of the human 505a proximate to the portion of subsurface vasculature 507a. The magnetic element 510a and pole 520a of the magnetic assembly 500a can be configured and/or operated to exert a time-dependent magnetic force on magnetic particles in the portion of subsurface vasculature 507a.

Further, the magnetic pole 520a could act to increase a property (e.g., a magnitude, a gradient magnitude) of the magnetic field produced by the magnetic assembly 500a in the portion of subsurface vasculature 507a and to decrease a property (e.g., a magnitude, a gradient magnitude) of the magnetic field produced by the magnetic assembly 500a in a region away from the body of the human 505a (i.e., to 'shield' the region below the magnetic assembly 500a from the magnetic field produced by the magnetic element 510a).

Figure 5B:
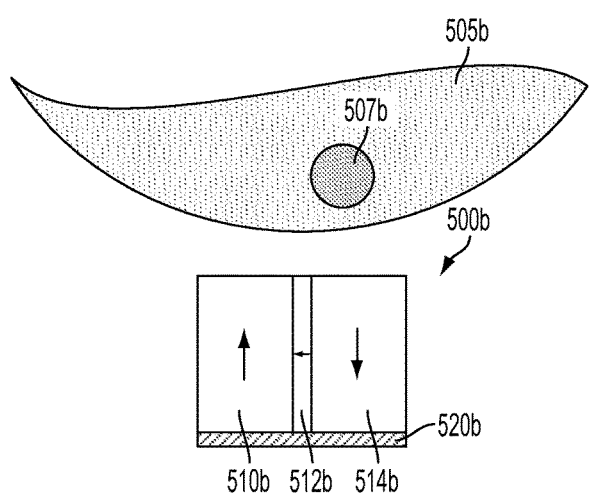
FIG. 5B is cross-sectional view of an example magnetic assembly, while positioned near a lumen of subsurface vasculature.

FIG. 5B illustrates a schematic diagram of an example magnetic assembly 500b comprising a plurality of magnetic elements 510b, 512b, 514b having respective magnetic moments (arrows) oriented such that the magnetic assembly forms a Halbach array. The magnetic assembly 500b additionally includes a magnetic pole 520b comprising a high-permeability material. The magnetic assembly 500b is positioned proximate to a portion of subsurface vasculature 507b within a body of a human 505b. The magnetic pole 520b comprises a layer of the high-permeability material disposed on a side of the magnetic assembly 500b opposite the human body 505b. The magnetic assembly 500b could be part of a wearable device and the wearable device could further include a mount configured to mount the wearable device to an external body surface of the body of the human 505b proximate to the portion of subsurface vasculature 507b. The magnetic elements 510b, 512b, 514b of the magnetic assembly 500b can be configured and/or operated to exert a time-dependent magnetic force on magnetic particles in the portion of subsurface vasculature 507b. The magnetic elements 510b, 512b, 514b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated.

Further, the magnetic pole 520b could act to increase a property (e.g., a magnitude, a gradient magnitude) of the magnetic field produced by the magnetic assembly 500b in the portion of subsurface vasculature 507b and to decrease a property (e.g., a magnitude, a gradient magnitude) of the magnetic field produced by the magnetic assembly 500b in a region away from the body of the human 505b (i.e., to 'shield' the region below the magnetic assembly 500b from the magnetic field produced by the magnetic elements 510b, 512b, 514b).

Figure 5C:
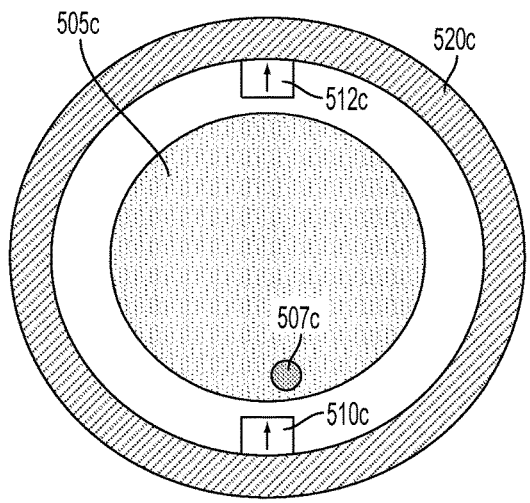
FIG. 5C is cross-sectional view of an example magnetic assembly, while positioned near a lumen of subsurface vasculature.

In some examples, the magnetic poles and/or magnetic elements of the magnetic assembly could wholly enclose an environment (e.g., a wrist or other body portion of a user). FIG. 5C illustrates a schematic diagram of an example magnetic assembly 500c comprising a plurality of magnetic elements (510c, 512c) having respective magnetic moments (arrows). The magnetic assembly 500c is positioned proximate to a portion of subsurface vasculature 507c within the body of a human 505c. The magnetic assembly 500c could be part of a wearable device and the wearable device could further include a mount configured to mount the wearable device to an external body surface of the body of the human 505c proximate to the portion of subsurface vasculature 507c. The magnetic assembly 500c wholly encloses a portion of the body of the human 507c with a magnetic pole 520c configured to transmit magnetic flux between the magnetic elements 510c, 512c to increase a property (e.g., a magnitude, a gradient magnitude) of the magnetic field produced by the magnetic assembly 500c in the portion of a subsurface vasculature 507c and to decrease a property (e.g., a magnitude, a gradient magnitude) of the magnetic field produced by the magnetic assembly 500c outside of the enclosing magnetic pole 520c (i.e., to 'shield' the region outside of the enclosing magnetic pole 520c).

Figure 5D:
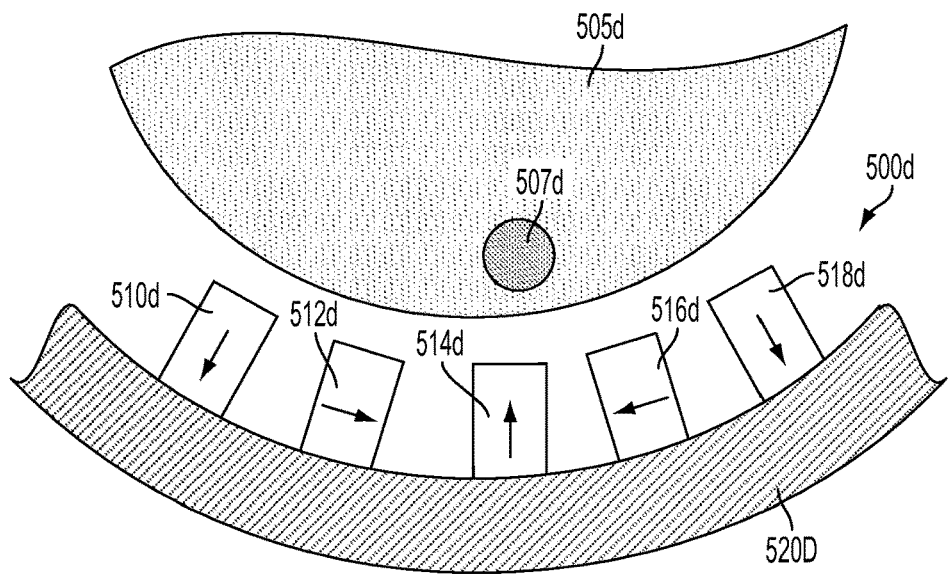
FIG. 5D is cross-sectional view of an example magnetic assembly, while positioned near a lumen of subsurface vasculature.

In some examples, the magnetic poles and/or magnetic elements of the magnetic assembly could partially enclose an environment (e.g., a wrist or other body portion of a user). FIG. 5D illustrates a schematic diagram of an example magnetic assembly 500d comprising a plurality of magnetic elements (510d, 512d, 514d, 516d, 518d) having respective magnetic moments (arrows). The magnetic assembly 500d is positioned proximate to a portion of subsurface vasculature 507d within a body of a human 505d. The magnetic assembly 500d could be part of a wearable device and the wearable device could further include a mount configured to mount the wearable device to an external body surface of the body of the human 505d proximate to the portion of subsurface vasculature 507d. The magnetic assembly 500d partially encloses a portion of the body of the human 507d with a magnetic pole 520d that is configured to increase a property (e.g., a magnitude, a gradient magnitude) of the magnetic field produced by the magnetic assembly 500d in the portion of subsurface vasculature 507d and to decrease a property (e.g., a magnitude, a gradient magnitude) of the magnetic field produced by the magnetic assembly 500d in a region away from the body of the human 505d (i.e., to 'shield' the region below the magnetic assembly 500d from the magnetic field produced by the magnetic elements 510d, 512d, 514d, 516d, 518d).

Figure 5E:
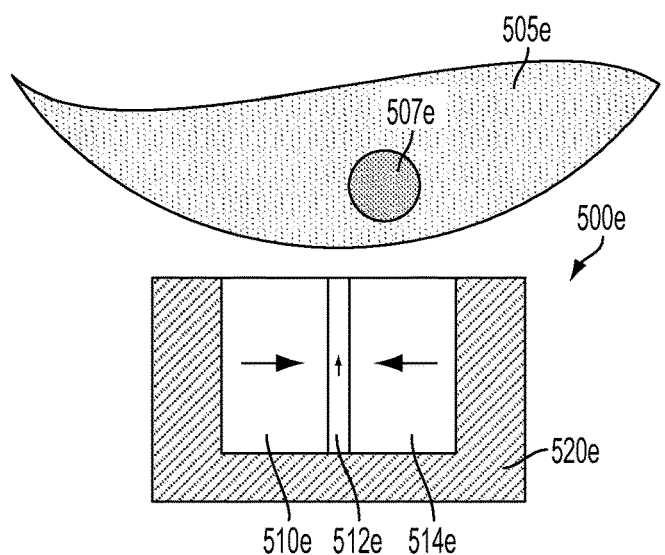
FIG. 5E is cross-sectional view of an example magnetic assembly, while positioned near a lumen of subsurface vasculature.

FIG. 5E illustrates a schematic diagram of an example magnetic assembly 500e comprising a plurality of magnetic elements 510e, 512e, 514e having respective magnetic moments (arrows) oriented such that the magnetic assembly forms a Halbach array, and such that a middle magnetic element 512e has a magnetic moment oriented toward a portion of subsurface vasculature 507e within a body of a human 505e. The magnetic assembly 500e additionally includes a magnetic pole 520e comprising a high-permeability material. The magnetic assembly 500e is positioned proximate to the portion of subsurface vasculature 507e within the body of the human 505e. The magnetic pole 520e comprises a layer of the high-permeability material disposed on at least three sides of the magnetic assembly 500e: opposite the human body 505e, opposite the left magnetic element 510e from the middle magnetic element 512e, and opposite the right magnetic element 514e from the middle magnetic element 512e. The magnetic assembly 500e could be part of a wearable device and the wearable device could further include a mount configured to mount the wearable device to an external body surface of the body of the human 505e proximate to the portion of subsurface vasculature 507e. The magnetic elements 510e, 512e, 514e of the magnetic assembly 500e can be configured and/or operated to exert a time-dependent magnetic force on magnetic particles in the portion of subsurface vasculature 507e.

The magnetic elements 510e, 512e, 514e being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated.

Further, the magnetic pole 520e could act to increase a property (e.g., a magnitude, a gradient magnitude) of the magnetic field produced by the magnetic assembly 500e in the portion of subsurface vasculature 507e and to decrease a property (e.g., a magnitude, a gradient magnitude) of the magnetic field produced by the magnetic assembly 500e in a region away from the body of the human 505e (i.e., to 'shield' the region below and/or to the sides of the magnetic assembly 500e from the magnetic field produced by the magnetic elements 510e, 512e, 514e).

In some embodiments, the magnetic assembly could have a narrowing geometry configured to concentrate a magnetic flux and/or to cause a magnetic field produced by the magnetic assembly to have a specified profile (i.e., a specified pattern of field magnitude, field direction, field gradient magnitude, field gradient direction) in one or more regions relative to the magnetic assembly. That is, an amount of flux and/or a magnitude of the magnetic field proximate to a narrow region of the narrowing geometry of the magnetic assembly (e.g., the 'top' peak of a truncated cone) could be greater than if the geometry did not narrow (e.g., the geometry was a cylinder, rather than a truncated cone). The narrowing geometry could include a magnetic pole and/or one or more permanent magnets. The narrowing geometry could be trapezoidal, conical, pyramidal, triangular, or some other narrowing geometry.

Figure 6A:
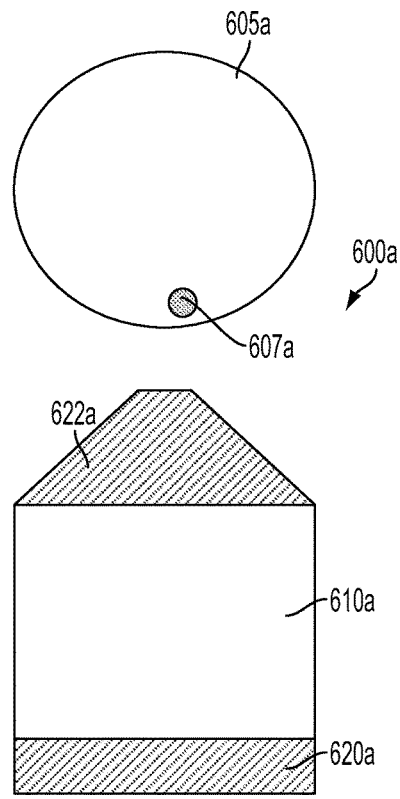
FIG. 6A is cross-sectional view of an example magnetic assembly, while positioned near a lumen of subsurface vasculature.

FIG. 6A illustrates a schematic diagram of an example magnetic assembly 600a comprising a magnetic flux source 610 and two magnetic poles 620a, 622a comprising a high-permeability material. The magnetic assembly 600a is positioned proximate to a portion of subsurface vasculature 607a within a body of a human 605a. The magnetic flux source 610a includes at least one permanent magnet, electromagnet or other magnetic flux-producing element. The magnetic flux source 610a can additionally include magnetic poles, air gaps, sensors, mechanically actuated elements (e.g., magnetic elements or other elements mounted to gears, gimbals, servos, or other actuators), or other components. In some examples, the magnetic flux source 610a could include a single magnetic element having a magnetic moment oriented toward the portion of subsurface vasculature 607a. In some examples, the magnetic flux source 610a could include a plurality of magnetic elements having respective magnetic moments oriented to form a Halbach array.

A first magnetic pole 620a comprises a layer of the high-permeability material disposed on a side of the magnetic assembly 600a opposite the human body 605a. A second (i.e., focusing) magnetic pole 622a comprises the high-permeability material disposed on a side of the magnetic assembly 600a toward the human body 605a. The second magnetic pole 622a could have one of a variety of narrowing geometries such that a first cross-sectional area of the second magnetic pole 622a proximate to the magnetic flux source 610a is greater than a second cross-sectional area of the second magnetic pole 622a farther from the magnetic flux source 610a (i.e., proximate to the human body 605a).

The magnetic assembly 600a could be part of a wearable device and the wearable device could further include a mount configured to mount the wearable device to an external body surface of the body of the human 605a proximate to the portion of subsurface vasculature 607a. The magnetic flux source 610a and magnetic poles 620a, 622a of the magnetic assembly 600a can be configured and/or operated to exert a time-dependent magnetic force on magnetic particles in the portion of subsurface vasculature 607a. Further, the magnetic poles 620a, 622a could act to increase a property (e.g., a magnitude, a gradient magnitude) of the magnetic field produced by the magnetic assembly 600a in the portion of subsurface vasculature 607a (e.g., proximate to a narrow end of the second magnetic pole 622a) and to decrease a property (e.g., a magnitude, a gradient magnitude) of the magnetic field produced by the magnetic assembly 600a in a region away from the body of the human 605a (i.e., to 'shield' the region below the magnetic assembly 600a from the magnetic field produced by the magnetic flux source 610a).

The second magnetic pole 622a could have a narrowing geometry chosen from a variety of narrowing geometries. The second magnetic pole 622a could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The second magnetic pole 622a could have a truncated narrowing geometry (e.g., a truncated cone, a truncated pyramid, a trapezoidal prism). The second magnetic pole 622a could have a narrowing cross-sectional shape in a plane substantially perpendicular an external body surface of the human 605a proximate to which the magnetic assembly 600a is positioned. For example, the second magnetic pole 622a could have a triangular cross-section, a trapezoidal cross-section, a partial elliptical cross-section, or some other narrowing shape cross-section.

Elements (e.g., 610a, 620a, 622a) of the magnetic assembly 600a could have specified properties (e.g., sizes, thicknesses, widths, lengths, compositions, shapes) chosen so as to optimize certain properties of the magnetic assembly (e.g., a magnetic field magnitude, a magnetic field gradient magnitude) given one or more constraints on the magnetic assembly (e.g., a maximum volume, a maximum mass, a specified permanent magnet geometry). In some examples, the geometry of the second (focusing) magnetic pole 622a could be specified to maximize the magnetic field magnitude and the magnetic field gradient magnitude proximate to the second magnetic pole 622a for a given small size of magnetic flux source 610a (e.g., a small permanent (e.g., Nd52) magnet). For example, the second magnetic pole 622a could have a length of 5 millimeters, a width of 5 millimeters, a thickness of 2 millimeters, and could have a truncated pyramid geometry wherein the flat top of the truncated pyramid had a width of 1 millimeter. In some examples, the second magnetic pole 622a could have a size and/or geometry relative to other elements of the magnetic assembly 600a such that the second magnetic pole 622a is magnetically saturated. Other geometries and dimensions of elements of a magnetic assembly are anticipated.

Figure 6B:
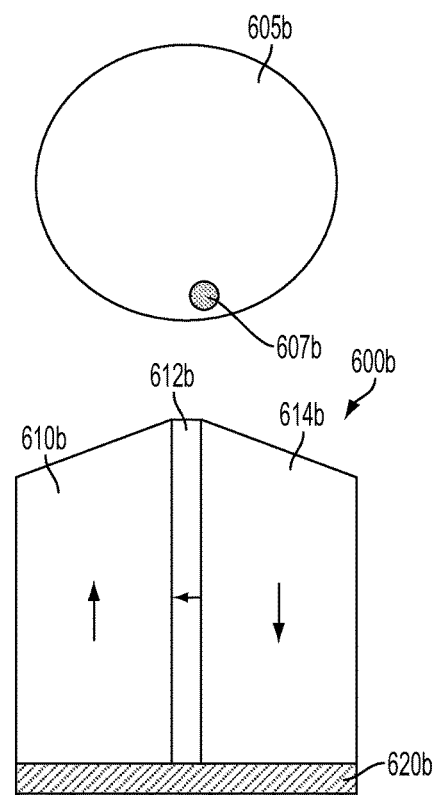
FIG. 6B is cross-sectional view of an example magnetic assembly, while positioned near a lumen of subsurface vasculature.

Additionally or alternatively, one or more permanent magnets of a magnetic assembly could have a narrowing geometry. FIG. 6B illustrates a schematic diagram of an example magnetic assembly 600b comprising a plurality of permanent magnets 610b, 612b, 614b having respective magnetic moments (arrows) that have, together, a narrowing geometry and whose magnetic moments are oriented such that the magnetic assembly forms a Halbach array. The magnetic assembly 600b additionally includes a magnetic pole 620a comprising a high-permeability material. The magnetic assembly 600b is positioned proximate to a portion of subsurface vasculature 607b within a body of a human 605b. The magnetic pole 620b comprises a layer of the high-permeability material disposed on a side of the magnetic assembly 600b opposite the human body 605b. The permanent magnets 610b, 612b, 614b could have one of a variety of narrowing geometries such that a cross-sectional shape of the permanent magnets 610b, 612b, 614b in a plane substantially perpendicular to an external body surface of the body of the human 605b proximate to the portion of subsurface vasculature 607b was narrower proximate to the external body surface.

The magnetic assembly 600b could be part of a wearable device and the wearable device could further include a mount configured to mount the wearable device to an external body surface of the body of the human 605b proximate to the portion of subsurface vasculature 607b. The permanent magnets 610b, 612b, 614b of the magnetic assembly 600b can be configured and/or operated to exert a time-dependent magnetic force on magnetic particles in the portion of subsurface vasculature 607b. The permanent magnets 610b, 612b, 614b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic assembly and/or an environment of interest proximate to the magnetic assembly are anticipated.

Further, the magnetic pole 620b could act to increase a property (e.g., a magnitude, a gradient magnitude) of the magnetic field produced by the magnetic assembly 600b in the portion of subsurface vasculature 607b and to decrease a property (e.g., a magnitude, a gradient magnitude) of the magnetic field produced by the magnetic assembly 600b in a region away from the body of the human 605b (i.e., to 'shield' the region below the magnetic assembly 600b from the magnetic field produced by the permanent magnets 610b, 612b, 614b).

The permanent magnets 610b, 612b, 614b could have a narrowing geometry chosen from a variety of narrowing geometries. The permanent magnets 610b, 612b, 614b could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The permanent magnets 610b, 612b, 614b could have a truncated narrowing geometry (e.g., a truncated cone, a truncated pyramid, a trapezoidal prism). The permanent magnets 610b, 612b, 614b could have a narrowing cross-sectional shape in a plane substantially perpendicular an external body surface of the human 605b proximate to which the magnetic assembly 600b is positioned. For example, the permanent magnets 610b, 612b, 614b could have a triangular cross-section, a trapezoidal cross-section, a partial elliptical cross-section, or some other narrowing shape cross-section.

Figure 7:
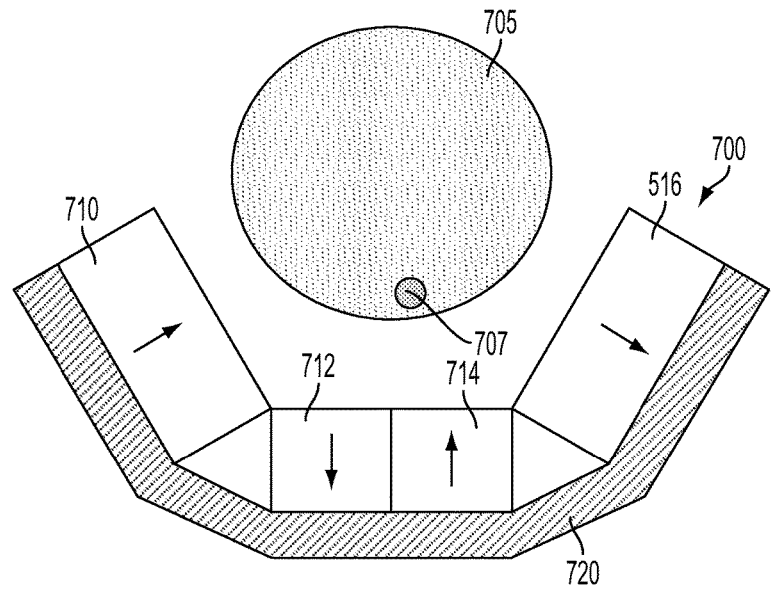
FIG. 7 is cross-sectional view of an example magnetic assembly, while positioned near a lumen of subsurface vasculature.

FIG. 7 illustrates a schematic diagram of an example magnetic assembly 700 comprising a magnetic pole 720 and a plurality of magnetic elements 710, 712, 714, 716 having respective magnetic moments (arrows). The magnetic assembly 700 is positioned proximate to a portion of subsurface vasculature 707 within a body of a human 705. The magnetic assembly 700 could be part of a wearable device and the wearable device could further include a mount configured to mount the wearable device to an external body surface of the body of the human 705 proximate to the portion of subsurface vasculature 707. The magnetic assembly 700 partially encloses a portion of the body of the human 707; that is, the magnetic elements 710, 712, 714, 716 are disposed on a concave surface of the magnetic assembly 700 and the concave surface is configured to partially enclose a convex surface (i.e., the external body surface) of the human 707.

The magnetic pole 720 is configured to increase a property (e.g., a magnitude, a gradient magnitude) of the magnetic field produced by the magnetic assembly 700 in the portion of subsurface vasculature 707 and to decrease a property (e.g., a magnitude, a gradient magnitude) of the magnetic field produced by the magnetic assembly 700 in a region away from the body of the human 705 (i.e., to 'shield' the region below the magnetic assembly 700 from the magnetic field produced by the magnetic elements 710, 712, 714, 716). First 710 and third 714 magnetic elements have magnetic moments pointing into respective proximate regions of the external body surface of the human 705 and third 712 and fourth 716 magnetic elements have magnetic moments pointing away from respective proximate regions of the external body surface of the human 705.

In some embodiments, the magnetic assembly could have magnetic elements (and magnetic moments thereof) configured according to a cylindrical, a spherical, an ellipsoidal, or some other three-dimensional geometry configured to produce a magnetic flux and/or to cause a magnetic field produced by the magnetic assembly to have a specified profile (i.e., a specified pattern of field magnitude, field direction, field gradient magnitude, field gradient direction) in one or more regions relative to the magnetic assembly. That is, while certain configurations of magnetic assemblies described herein (e.g., 100a, 200a, 200b, 400a, 400b, 40c, 400d, 500a, 500b, 500c, 500d, 500e, 600b, 700) include magnetic elements having substantially planar configurations, magnetic elements and/or other components of a magnetic assembly could be configured in other ways.

Figure 8A:
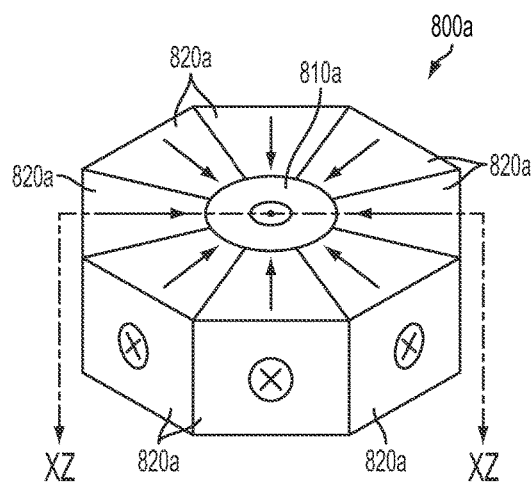
FIG. 8A is perspective view of an example magnetic assembly.

FIG. 8A illustrates a perspective view of an example magnetic assembly 800a having an axial magnetic element 810a and a plurality of radial magnetic elements 820a. The axial magnetic element 810a has a magnetic moment directed upward (illustrated by the dot-in-circle symbol to indicate that the magnetic moment is directed out of the illustrated surface of the axial magnetic element 810a), parallel to a central axis of the axial magnetic element 810a. The radial magnetic elements 820b are disposed proximate to and surrounding the axial magnetic element 810a and have respective magnetic moments oriented toward the central axis of the axial magnetic element 810a (illustrated by arrows and by the cross-in-circle symbol to indicate that the magnetic moment is directed into the illustrated surfaces of the radial magnetic elements 820a).

Figure 8B:
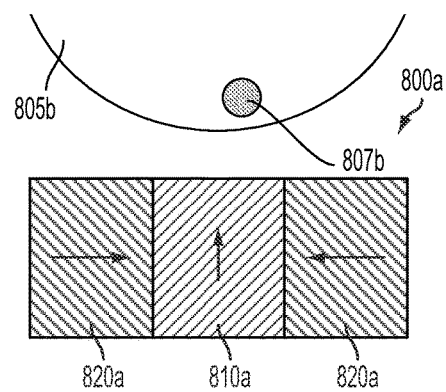
FIG. 8B is cross-sectional view of the example magnetic assembly illustrated in FIG. 8A.

FIG. 8B illustrates a cross-sectional schematic diagram of the example magnetic assembly 800a taken though plane XZ illustrated in FIG. 8A. The magnetic moments of the axial magnetic element 810a and two radial magnetic elements 820a are shown (arrows). The magnetic assembly 800a is positioned proximate to a portion of subsurface vasculature 807a within a body of a human 805a. The magnetic assembly 800a could be part of a wearable device and the wearable device could further include a mount configured to mount the wearable device to an external body surface of the body of the human 805a proximate to the portion of subsurface vasculature 807a.

The number, shape, disposition, and other properties of the magnetic assembly 800a are intended as a non-limiting example of a magnetic assembly having elements (e.g., magnetic elements having respective magnetic moments) disposed in three dimensions. Other such magnetic assemblies are anticipated. Further, the overall shape of such magnetic assemblies could be flattened (e.g., the shape of individual radial magnetic elements could vary such that the magnetic assembly had an overall flatter shape) such that such magnetic assemblies could be tightly packed into a space. A greater or fewer number of radial magnetic elements could be included. A magnetic assembly could include multiple rings or rows of radial magnetic elements (e.g., the example magnetic assembly 800a could further include an outside ring of magnetic elements having respective magnetic moments oriented, e.g., antiparallel to the magnetic moment of the axial magnetic segment 810a) or additional magnetic elements formed, disposed, or otherwise configured according to some other design.

Figure 8C:
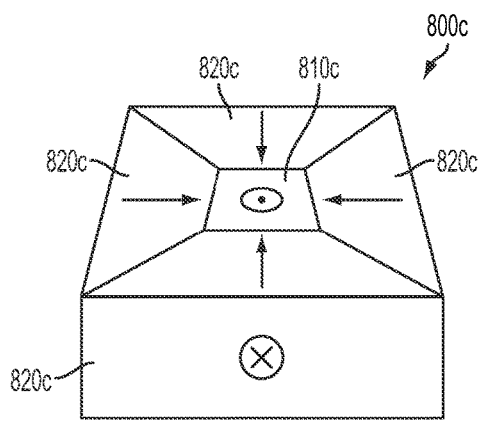
FIG. 8C is perspective view of an example magnetic assembly.

For example, FIG. 8C illustrates a perspective view of an example magnetic assembly 800c having a square-shaped axial magnetic element 810c and four trapezoidally-shaped radial magnetic elements 820c. The axial magnetic element 810c has a magnetic moment directed upward (illustrated by the dot-in-circle symbol to indicate that the magnetic moment is directed out of the illustrated surface of the axial magnetic element 810c), parallel to a central axis of the axial magnetic element 810c. The radial magnetic elements 820c are disposed proximate to and surrounding the axial magnetic element 810c and have respective magnetic moments oriented toward the central axis of the axial magnetic element 810c (illustrated by arrows and by the cross-in-circle symbol to indicate that the magnetic moment is directed into the illustrated surface of the radial magnetic elements 820c).

Figure 8D:
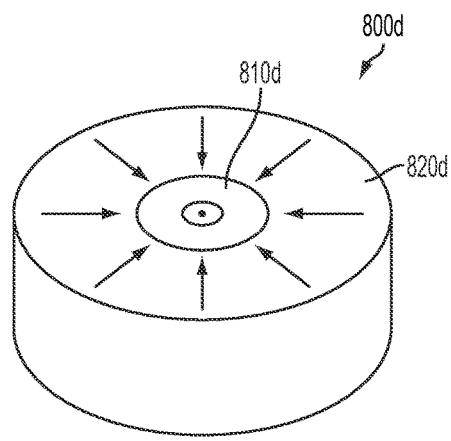
FIG. 8D is perspective view of an example magnetic assembly.

In another example, FIG. 8D illustrates a perspective view of an example magnetic assembly 800d having a cylindrical axial magnetic element 810d and a ring-shaped radial magnetic element 820d. The axial magnetic element 810d has a magnetic moment directed upward (illustrated by the dot-in-circle symbol to indicate that the magnetic moment is directed out of the illustrated surface of the axial magnetic element 810d), parallel to a central axis of the axial magnetic element 810d. The radial magnetic element 820d is disposed proximate to and surrounding the axial magnetic element 810d and magnetic domains of the radial magnetic element 820d are configured such that local magnetic moments of regions within the radial magnetic element 820d are oriented toward the central axis of the axial magnetic element 810a (arrows). The radial magnetic element 820d could be configured in this way by adhering or otherwise forming together a plurality of magnetic elements (e.g., a plurality of thin, truncated-wedge-shaped slices of magnetized magnetic material), by manipulating the orientation of the magnetic moment of magnetic domains within a single ring-shaped piece of magnetic material, or by some other method(s).

Further, such magnetic assemblies could be composed of magnetic segments that are separated by respective specified distances. The configuration of a magnetic assembly in such a way could increase a magnitude of a magnetic field and/or a magnetic field gradient produced by a given mass, area, or other amount of magnetic material by introducing edge and/or fringe field effects at the edges of the magnetic segments (e.g., in the spaces between the magnetic segments). As a result, a magnetic assembly that includes a given mass of magnetic material configured as a linear array of magnetic segments (as described herein) could exert a greater attracted magnetic force (e.g., on magnetic particles in a portion of subsurface vasculature proximate to the magnetic assembly) than a magnetic assembly that includes a same mass of magnetic material that is not configured as a plurality of magnetic segments.

Magnetic segments of a magnetic assembly could be configured in a variety of ways, as described herein or otherwise. Magnetic segments could be repeated (i.e., the configuration of two or more magnetic segments could be substantially the same), could be individual, or some combination thereof. An individual magnetic segment could be configured similarly to one or more of the magnetic assemblies described herein (e.g., 120a, 120b, 120c, 120d, 200, 300a, 300c, 400a, 400b, 400c, 400d, 500a, 500b, 500c, 500d, 500e, 600a, 600b, 700, 800a, 800c, 800d). A spacing or other property of a linear or other array of such segments could be controlled in a time-dependent way such that a magnetic force exerted by such a magnetic assembly could be controlled related to the controlled spacing or other property.

Magnetic assemblies, devices containing magnetic assemblies, magnetic particles, and other aspects and embodiments described herein (e.g., 120a, 120b, 120c, 120d, 200, 300a, 300c, 400a, 400b, 400c, 400d, 500a, 500b, 500c, 500d, 500e, 600a, 600b, 700, 800a, 800c, 800d) could be configured and/or operated to provide a variety of applications. In some examples, magnetic particles could be configured to bind to an analyte of interest, and a magnetic assembly (e.g., a magnetic assembly configured and/or operable to exert a time-dependent magnetic force) could be configured to collect, release, separate, modify, or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle). Other configurations, operations, and applications of the embodiments described herein are anticipated.

IV. EXAMPLE METHODS

Figure 9:
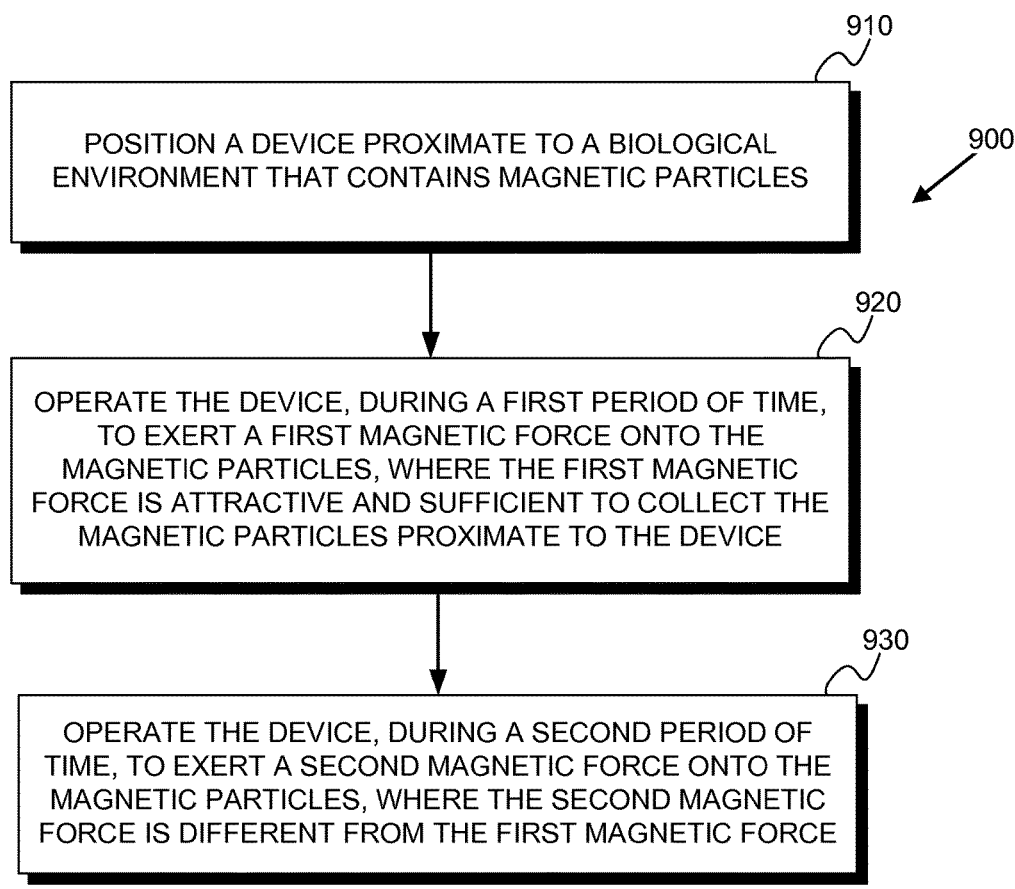
FIG. 9 is a flowchart of an example method

FIG. 9 is a flowchart of an example method 900 for exerting a time-dependent magnetic force on magnetic particles in a biological environment using a device. The method 900 includes positioning the wearable device proximate to the biological environment containing the magnetic particles 910. This could include operating a mount included in the device that is configured to secure the wearable device at a specified location relative to the portion of subsurface vasculature. For example, the biological environment could be a body of the wearer and the mount could be configured to enclose a wrist, an ankle, a chest, or some other aspect of the body of the wearer. In some examples, this could include positioning the device relative to a visible or other landmark on or beneath an external body surface (e.g., a tattoo, a visible artery or vein, bony protuberance, a joint, a birth mark). In some examples, this could include manipulating and/or changing the location of the device relative to some indication from the device, e.g., and indication from the wearable device that the magnetic assembly was located proximate to a target portion of subsurface vasculature.

The method 900 additionally includes operating the device, during a first period of time, to exert a first magnetic force onto the magnetic particles, where the first magnetic force is attractive and sufficient to collect the magnetic particles proximate to the device 920. This could include exerting an attractive force on the magnetic particles sufficient to collect the magnetic particles in a portion of subsurface vasculature proximate to the device. This could include applying a first specified current and/or voltage to an electromagnet of the device. Other examples of exerting a first magnetic force on magnetic particles using the device and applications thereof as described herein and otherwise are anticipated.

The method 900 additionally includes operating the device, during a second period of time, to exert a second magnetic force onto the magnetic particles, where the second magnetic force is different than the first magnetic force 930. This could include exerting an attractive force on the magnetic particles sufficient to collect the magnetic particles in a portion of subsurface vasculature proximate to the device. This could include applying a second specified current and/or voltage to an electromagnet of the device. This could include changing a configuration of one or more elements of the device (e.g., translating, rotating, or otherwise actuating one or more permanent magnets, electromagnets, magnetic shims, or other elements of the device) between the first and second periods of time such that the first and second exerted magnetic forces are different. Other examples of exerting a second magnetic force on magnetic particles using the device and applications thereof as described herein and otherwise are anticipated.

The method 900 could include additional steps or elements. For example, the method 900 could include introducing the magnetic particles into the biological environment (e.g., into a portion of subsurface vasculature by injecting, ingesting, transdermally transferring, or otherwise introducing the engineered particles into a lumen of vasculature of a human). In some examples, the magnetic particles could be configured to bind to an analyte and to enable detection of one or more properties of, modification of one or more properties of, and/or some other interaction with the analyte.

In some examples, the method 900 could include detecting one or more properties of an analyte to which the first and/or second magnetic particles are configured to bind. This could include operating a detector of the wearable device to detect the one or more properties of the bound analyte. In some examples, this could include exerting an attractive magnetic force on the magnetic particles such that the magnetic particles and instances of the analyte bound thereto are caused to collect proximate to the magnetic assembly and/or the detector of the device. Other methods of detecting one or more properties of an analyte using a device configured as described herein and positioned proximate to a biological environment of interest (e.g., a portion of subsurface vasculature) are anticipated.

In some examples, the method 900 could include extracting the magnetic particles from the biological environment. For example, a hypodermic needle could be inserted into a portion of subsurface vasculature (i.e., the biological environment) and a plunger or other element of the hypodermic needle could be operated to extract the blood containing the magnetic particles from the portion of subsurface vasculature. In another example, the end of a catheter or some other temporarily or semi-permanently placed tube could be disposed in the portion of subsurface vasculature such that the magnetic particles could be extracted continuously, over a period of time.

V. EXAMPLE WEARABLE DEVICES

A wearable device 1000 can measure a plurality of physiological parameters of a person wearing the device, among other functions. Some or all of the functions of the wearable device 1000 are enabled by collection, release, separation, or some other manipulation of magnetic particles in blood of the wearer of the device. Such manipulations can be effected by the exertion of time-dependent magnetic forces on the magnetic particles by a magnetic assembly (e.g., 120a, 120b, 120c, 120d, 200, 300a, 300c, 400a, 400b, 400c, 400d, 500a, 500b, 500c, 500d, 500e, 600a, 600b, 700, 800a, 800c, 800d) disposed on or in the wearable device 1000. The term "wearable device," as used in this disclosure, refers to any device that is capable of being worn at, on or in proximity to a body surface, such as a wrist, ankle, waist, chest, or other body part.

Figure 10:
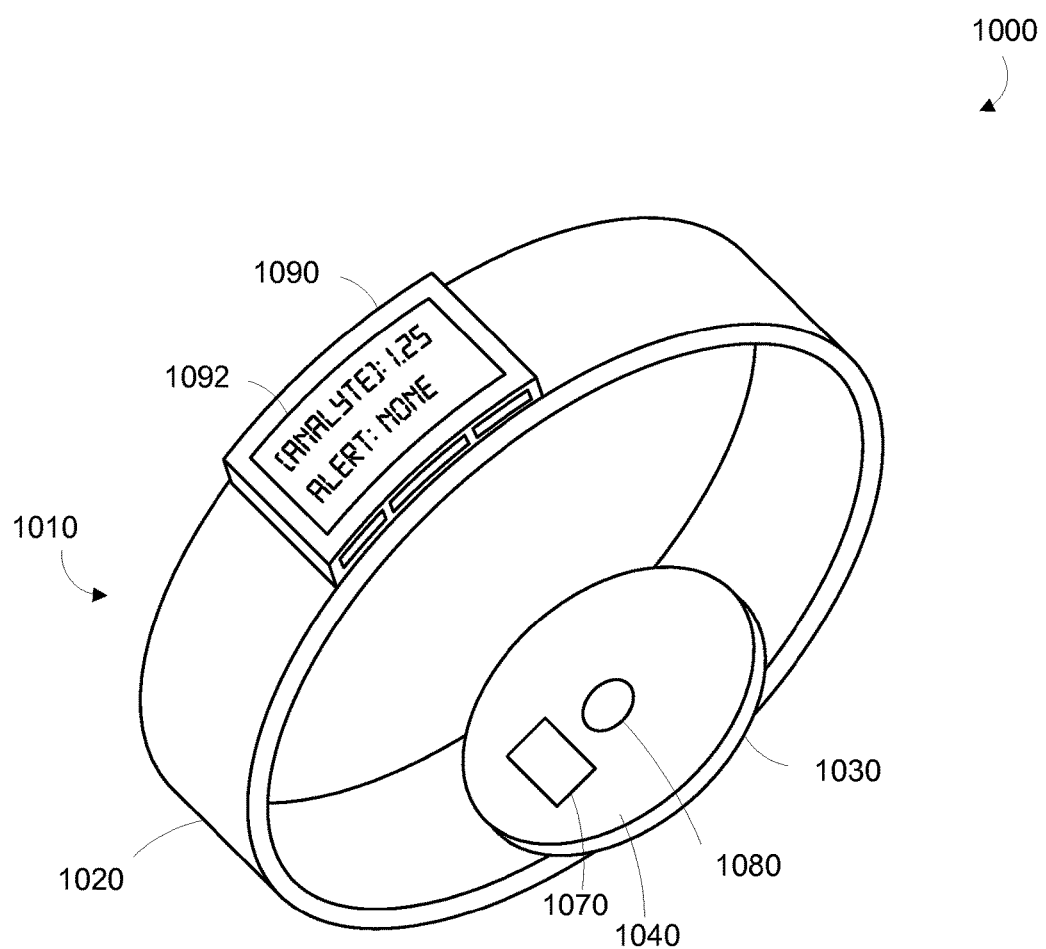
FIG. 10 is a perspective view of an example wearable device.

In order to manipulate magnetic particles and/or take in vivo measurements in a non-invasive manner from outside of the body, the wearable device may be positioned on a portion of the body where subsurface vasculature containing magnetic particles is easily affectable (e.g., by exertion of time-dependent magnetic forces) and observable, depending on the type of modification and detection systems used. The device may be placed in close proximity to the skin or tissue, but need not be touching or in intimate contact therewith. A mount 1010, such as a belt, wristband, ankle band, etc. can be provided to mount the device at, on or in proximity to the body surface. The mount 1010 may prevent the wearable device 1000 from moving relative to the body to ensure effective manipulation of magnetic particles and/or detection of one or more physiological properties of the wearer. In one example, shown in FIG. 10, the mount 1010, may take the form of a strap or band 1020 that can be worn around a part of the body. Further, the mount 1010 may include an adhesive material for adhering the wearable device 1000 to the body of a wearer.

A manipulation platform 1030 is disposed on the mount 1010 such that it can be positioned on the body where subsurface vasculature is easily affected. An inner face 1040 of the manipulation platform 1030 is intended to be mounted facing to the body surface. The manipulation platform 1030 may house a magnetic assembly 1080. In such embodiments, the magnetic assembly 1080 could be configured to separate collect, separate, release, or otherwise manipulate particles in a portion of subsurface vasculature by exerting time-dependent magnetic forces on the magnetic particles. Manipulation of the magnetic particles through the exertion of time-dependent magnetic forces could take the form of one or more of the varieties of manipulation described herein (e.g., in combination with FIGS. 1A-D) and could include operation and/or actuation of elements of the magnetic assembly 1080 as described herein (e.g., in connection with FIGS. 2A-2E and/or FIGS. 3A-3D). The magnetic assembly 1080 could include electromagnets, permanent magnets, magnetic segments, spacers, magnetic shims, or other magnetic or non-magnetic material configured in a variety of ways (e.g., configured similarly to magnetic assemblies 120a, 120b, 120c, 120d, 200, 300a, 300c, 400a, 400b, 400c, 400d, 500a, 500b, 500c, 500d, 500e, 600a, 600b, 700, 800a, 800c, 800d).

In some examples, the wearable device 1000 further includes at least one detector 1070 for detecting at least one physiological parameter, which could include any parameters that may relate to the health of the person wearing the wearable device. For example, the detector 1070 could be configured to measure blood pressure, pulse rate, respiration rate, skin temperature, etc. At least one of the detectors 1070 could be configured to non-invasively measure one or more properties of magnetic particles in blood and/or analytes bound thereto circulating in subsurface vasculature proximate to the wearable device. In a non-exhaustive list, detector 1070 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor. Operation of the detector 1070 could be related to and/or contingent on collection, separation, release, or some other manipulation of magnetic particles by the magnetic assembly 1080.

The wearable device 1000 may also include a user interface 1090 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 1090 may include a display 1092 where a visual indication of the alert or recommendation may be displayed. The display 1092 may further be configured to provide an indication the battery status of the device or the status of the modification system or an indication of any measured physiological parameters, for instance, the concentrations of certain blood analytes being measured.

Figure 11A:
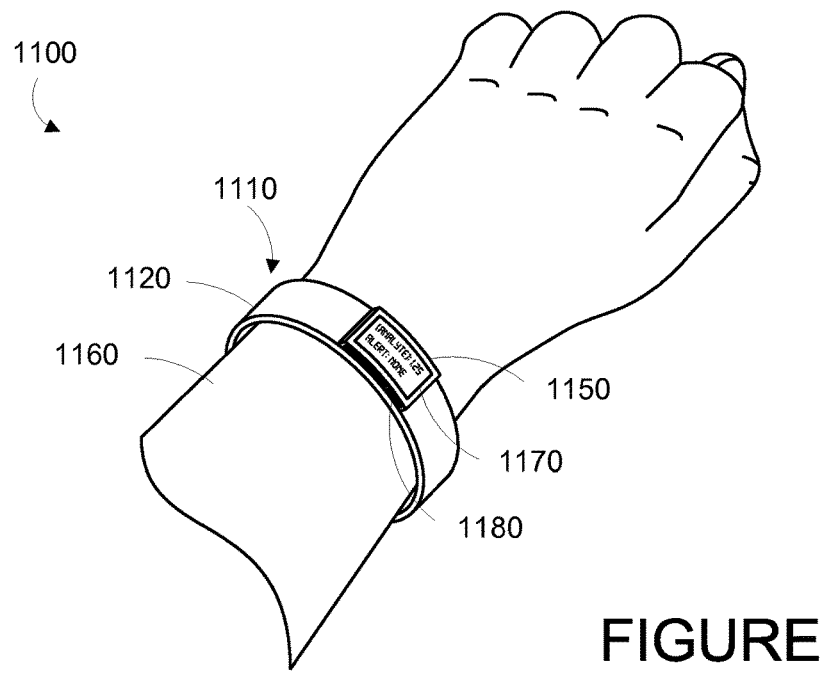
FIG. 11A is a perspective top view of an example wrist-mounted device, when mounted on a wearer's wrist.
Figure 11B:
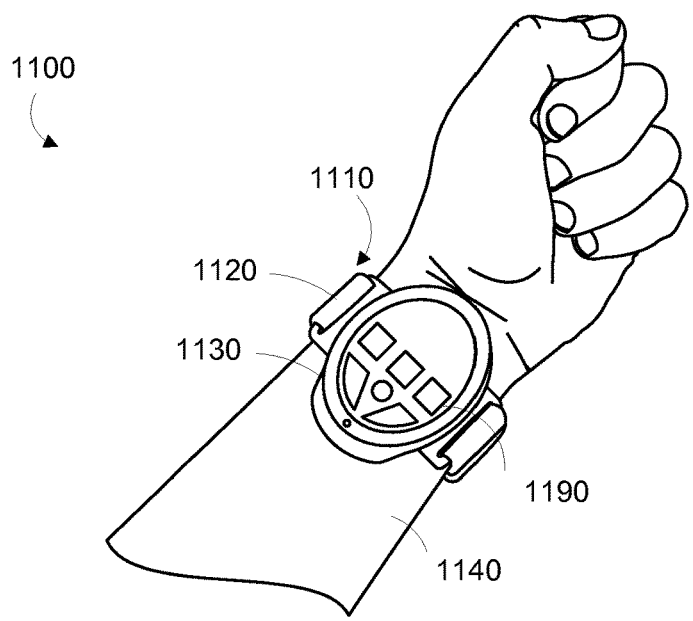
FIG. 11B is a perspective bottom view of the example wrist-mounted device shown in FIG. 11A, when mounted on a wearer's wrist.

In one example, the wearable device is provided as a wrist-mounted device, as shown in FIGS. 11A and 11B. The wrist-mounted device may be mounted to the wrist of a living subject with a wristband or cuff, similar to a watch or bracelet. As shown in FIGS. 11A and 11B, the wrist mounted device 1100 may include a mount 1110 in the form of a wristband 1120, a manipulation platform 1130 positioned on the anterior side 1140 of the wearer's wrist, and a user interface 1150 positioned on the posterior side 1160 of the wearer's wrist. The wearer of the device may receive, via the user interface 1150, one or more recommendations or alerts generated either from a remote server or other remote computing device, or alerts based on physiological properties of a wearer detected by the wrist-mounted device 1100. Such a configuration may be perceived as natural for the wearer of the device in that it is common for the posterior side 1160 of the wrist to be observed, such as the act of checking a wrist-watch. Accordingly, the wearer may easily view a display 1170 on the user interface. Further, the manipulation platform 1130 may be located on the anterior side 1140 of the wearer's wrist where the subsurface vasculature may be readily affectable. However, other configurations are contemplated.

The display 1170 may be configured to display a visual indication of the alert or recommendation and/or an indication of the status of the wearable device and an indication of measured physiological parameters, for instance, the concentrations of certain target blood analytes bound to collected, separated, released, or otherwise magnetically manipulated magnetic particles in the blood. Further, the user interface 1150 may include one or more buttons 1180 for accepting inputs from the wearer. For example, the buttons 1180 may be configured to change the text or other information visible on the display 1170. As shown in FIG. 11B, manipulation platform 1130 may also include one or more buttons 1190 for accepting inputs from the wearer. The buttons 1190 may be configured to accept inputs for controlling aspects of the wrist-mounted device 1100, such as inputs indicating the wearer's current health state (i.e., normal, migraine, shortness of breath, heart attack, fever, "flu-like" symptoms, food poisoning, etc.).

VI. CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

While various aspects and embodiments herein are described in connection with exerting forces on magnetic particles disposed in particular example biological environments (e.g., a portion of subsurface vasculature), other applications and environments are possible. Aspects and embodiments herein could be applied to exert forces on magnetic particles in in vivo or in vitro human or animal tissues, a fluid in a scientific, medical, or industrial testing process, or some other environment. Magnetic forces could be exerted on magnetic particles disposed in a natural environment, e.g., a lake, river, stream, marsh, or other natural locale. Magnetic forces could be exerted on magnetic particles disposed in a fluid environment of an industrial process or other artificial environment, e.g., a water treatment process, a food preparation process, a pharmaceutical synthesis process, a chemical synthesis process, a brewing and/or distilling process, or other artificial locale. Magnetic forces could be exerted on magnetic particles disposed in an environment that includes a flowing fluid (e.g., fluid flowing in a blood vessel, a pipe, a culvert) and/or a substantially static fluid. Other environments and applications of aspects and embodiments described herein are anticipated.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method, comprising:
    positioning a device proximate to a biological environment that contains magnetic particles that are configured to selectively interact with an analyte of interest;
    operating the device, during a first period of time, to collect, by way of exerting a first magnetic force, at least one of the magnetic particles in the biological environment, wherein the first magnetic force is an attractive magnetic force that is sufficient to collect the at least one of the magnetic particles in the biological environment proximate to the device; and
    operating the device, during a second period of time, to exert a second magnetic force onto the magnetic particles in the biological environment, wherein the second magnetic force is different from the first magnetic force, and wherein the second magnetic force is sufficiently less than the first magnetic force that one or more of the magnetic particles collected proximate to the device during the first period of time are released during the second period of time;
    wherein the device comprises a detector, and further comprising: detecting one or more properties of the analyte of interest from the collected magnetic particles using the detector.

2. The method of claim 1, further comprising introducing the magnetic particles into the biological environment.

3. The method of claim 1, wherein the biological environment is a portion of subsurface vasculature proximate to an external body surface, and wherein positioning the device proximate to the biological environment comprises positioning the device on the external body surface.

4. The method of claim 1, wherein the device comprises at least one electromagnet, wherein operating the device during the first and second periods of time to exert first and second magnetic forces, respectively, comprises operating the at least one electromagnet of the device to exert the first and second magnetic forces on the magnetic particles.

5. The method of claim 1, wherein the device comprises at least one permanent magnet, wherein the first and second magnetic forces are caused by respective first and second magnetic fields produced by the at least one permanent magnet of the device during the first and second time periods, respectively.

6. The method of claim 5, further comprising moving the at least one permanent magnet of the device relative to the biological environment, wherein moving the at least one permanent magnet is performed between the first and second periods of time, wherein moving the at least one permanent magnet causes the second magnetic force to be less than the first magnetic force.

7. The method of claim 5, wherein the device further comprises a magnetic shim material, and further comprising:
    moving the magnetic shim material relative to the at least one permanent magnet and the biological environment, wherein moving the magnetic shim material is performed between the first and second periods of time, wherein moving the magnetic shim material causes the second magnetic force to be less than the first magnetic force.

8. The method of claim 5, wherein the at least one permanent magnet comprises a plurality of permanent magnets, wherein individual permanent magnets of the plurality of permanent magnets have respective magnetic moments, wherein the magnetic moments of the plurality of permanent magnets have a first configuration during the first period of time and a second configuration during the second period of time such that the second magnetic force is less than the first magnetic force, and further comprising:
rotating the magnetic moments of at least two permanent magnets of the plurality of permanent magnets, wherein rotating the magnetic moments is performed between the first and second periods of time, and wherein rotating the magnetic moments causes the configuration of the magnetic moments of the plurality of permanent magnets to change between the first configuration and the second configuration.

9. The method of claim 1, further comprising:
extracting at least one of the collected at least one magnetic particle from the biological environment.

10. The method of claim 1, wherein the magnetic particles that are collected proximate to the device during the first period of time comprise a plug of magnetic particles, wherein the plug of magnetic particles has a rate of interaction with the analyte of interest that is related to the first and second magnetic forces such that the plug of magnetic particles has first and second rates of interaction during respective first and second periods of time, and wherein the second rate of interaction is higher than the first rate of interaction.

11. An apparatus, comprising:
a magnetic field producer, wherein the magnetic field producer is configured to be positioned proximate to an external body surface that is proximate to a portion of subsurface vasculature containing magnetic particles belonging to a specified set of magnetic particles, wherein the magnetic particles are configured to selectively interact with an analyte of interest, wherein the magnetic field producer is configured to exert first and second magnetic forces onto the magnetic particles during respective first and second periods of time, wherein the first magnetic force is an attractive magnetic force that is sufficient to collect, during the first period of time, at least one of the magnetic particles in the portion of subsurface vasculature proximate to the device, wherein the second magnetic force is different from the first magnetic force, and wherein the second magnetic force is sufficiently less than the first magnetic force that one or more of the magnetic particles collected proximate to the device during the first period of time are released during the second period of time, and
a detector configured to detect one or more properties of the analyte of interest from the collected particles.

12. The apparatus of claim 11, wherein the apparatus further comprises:
a mount configured to mount the magnetic field producer proximate to the external body surface.

13. The apparatus of claim 11, wherein the magnetic field producer comprises at least one permanent magnet.

14. The apparatus of claim 13, wherein the apparatus is configured to move the at least one permanent magnet relative to the portion of subsurface vasculature between the first period of time and the second period of time, wherein moving the at least one permanent magnet between the first period of time and the second period of time causes the second magnetic force to be less than the first magnetic force.

15. The apparatus of claim 13, further comprising a magnetic shim comprised of magnetic shim material, wherein the apparatus is configured to move the magnetic shim relative to the portion of subsurface vasculature between the first period of time and the second period of time, wherein moving the magnetic shim between the first period of time and the second period of time causes the second magnetic force to be less than the first magnetic force.

16. The apparatus of claim 13, wherein the at least one permanent magnet comprises a plurality of permanent magnets, wherein individual permanent magnets of the plurality of permanent magnets have respective magnetic moments, wherein the magnetic moments of the plurality of permanent magnets have a first configuration during the first period of time and a second configuration during the second period of time such that the second magnetic force is less than the first magnetic force, wherein the apparatus is configured to rotate the magnetic moments of at least two permanent magnets of the plurality of permanent magnets between the first period of time and the second period of time, and wherein rotating the magnetic moments between the first period of time and the second period of time causes the configuration of the magnetic moments of the plurality of permanent magnets to change between the first configuration and the second configuration.

* * * * *